(12) United States Patent
Herweck et al.

(10) Patent No.: US 9,801,982 B2
(45) Date of Patent: *Oct. 31, 2017

(54) IMPLANTABLE BARRIER DEVICE

(75) Inventors: Steve A. Herweck, Nashua, NH (US); Joseph Ferraro, Londonderry, NH (US); Paul Martakos, Pelham, NH (US); Theodore Karwoski, Hollis, NH (US); Anthony Richard Horton, Manchester, NH (US)

(73) Assignee: Atrium Medical Corporation, Merrimack, NH (US)

( * ) Notice: Subject to any disclaimer, the term of this patent is extended or adjusted under 35 U.S.C. 154(b) by 572 days.

This patent is subject to a terminal disclaimer.

(21) Appl. No.: 12/075,223

(22) Filed: Mar. 10, 2008

(65) Prior Publication Data

US 2008/0206305 A1    Aug. 28, 2008

Related U.S. Application Data

(63) Continuation-in-part of application No. 11/237,420, filed on Sep. 28, 2005, and a continuation-in-part of application No. 11/980,155, filed on Oct. 30, 2007.

(60) Provisional application No. 60/613,808, filed on Sep. 28, 2004, provisional application No. 60/856,983, filed on Nov. 6, 2006.

(51) Int. Cl.
| | |
|---|---|
| *A61L 31/10* | (2006.01) |
| *A61F 2/00* | (2006.01) |
| *A61L 31/14* | (2006.01) |
| *A61F 2/06* | (2013.01) |

(52) U.S. Cl.
CPC ............ *A61L 31/10* (2013.01); *A61F 2/0063* (2013.01); *A61L 31/145* (2013.01); *A61F 2/06* (2013.01); *A61F 2250/0067* (2013.01)

(58) Field of Classification Search
None
See application file for complete search history.

(56) References Cited

U.S. PATENT DOCUMENTS

| | | | |
|---|---|---|---|
| 1,948,959 A * | 2/1934 | Croce | 106/222 |
| 2,368,306 A | 1/1945 | Kiefer et al. | |
| 2,403,458 A * | 7/1946 | Ransom et al. | 554/206 |
| 2,735,814 A | 2/1956 | Hodson et al. | |
| 2,986,540 A | 5/1961 | Posnansky | |
| 3,464,413 A | 9/1969 | Goldfarb et al. | |
| 3,556,294 A | 1/1971 | Walck et al. | |
| 3,567,820 A | 3/1971 | Sperti | |
| 3,803,109 A | 4/1974 | Nemoto et al. | |
| 3,967,728 A | 7/1976 | Gordon et al. | |
| 4,308,120 A | 12/1981 | Pennewiss et al. | |
| 4,323,547 A | 4/1982 | Knust et al. | |
| 4,447,418 A | 5/1984 | Maddoux | |
| 4,557,925 A | 12/1985 | Lindahl et al. | |
| 4,664,114 A | 5/1987 | Ghodstain | |
| 4,813,210 A | 3/1989 | Masuda et al. | |
| 4,814,329 A | 3/1989 | Harsanyi et al. | |
| 4,847,301 A | 7/1989 | Murray | |
| 4,880,455 A | 11/1989 | Blank | |
| 4,883,667 A | 11/1989 | Eckenhoff | |
| 4,886,787 A | 12/1989 | De Belder et al. | |
| 4,894,231 A | 1/1990 | Moreau et al. | |
| 4,895,724 A | 1/1990 | Cardinal et al. | |
| 4,911,707 A | 3/1990 | Heiber et al. | |
| 4,937,254 A | 6/1990 | Sheffield et al. | |
| 4,938,763 A | 7/1990 | Dunn et al. | |
| 4,941,308 A | 7/1990 | Grabenkort et al. | |
| 4,947,840 A * | 8/1990 | Yannas et al. | 602/50 |
| 4,952,419 A | 8/1990 | De Leon | |
| 4,968,302 A | 11/1990 | Schluter et al. | |
| 5,017,229 A | 5/1991 | Burns et al. | |
| 5,061,281 A | 10/1991 | Mares et al. | |
| 5,132,115 A | 7/1992 | Wolter et al. | |
| 5,147,374 A | 9/1992 | Fernandez et al. | |
| 5,151,272 A | 9/1992 | Engstrom et al. | |

(Continued)

FOREIGN PATENT DOCUMENTS

| | | |
|---|---|---|
| EP | 0 471 566 | 2/1992 |
| EP | 0 610 731 A1 | 8/1994 |

(Continued)

OTHER PUBLICATIONS

Morse Industrial and Engineering Chemistry 1941 33:1039-1043.*
Mallegol et al. Progress in Organic Coatings 2000 39:107-113.*
By Timar-Balzsy et al. Chemical Principles of Textile Conservation. Oxford: Elsevier Science Ltd., 1998. 117-119.*
Mallegol et al. Journal of the American Oil Chemists' Society 2000 77:257-263.*
Wicks et al. Organic Coatings:Science and Technology 1999 New York:Wiley Interscience p. 258-267.*
Mills et al. Oils and Fats. "The Organic Chemistry of Museum Objects" London:Buttersworth and Co. 1987, p. 26-40.*
Erhardt Paints Based on Drying Oil Media. Painted Wood: History & Conservation. Ed. Berland Singapore: The J. Paul Getty Trust 1998. p. 17-32.*

(Continued)

*Primary Examiner* — Robert A Wax
*Assistant Examiner* — Caralynne Helm
(74) *Attorney, Agent, or Firm* — Wesley Scott Ashton

(57) ABSTRACT

A barrier device is formed of a barrier component that can exhibit anti-inflammatory properties, non-inflammatory properties, and/or adhesion-limiting properties, as well as generate a modulated healing effect on injured tissue. The barrier component can be a non-polymeric cross-linked gel derived at least in part from a fatty acid compound, and may include a therapeutic agent. The barrier device can have anchoring locations to provide an area on the barrier device to interface with an anchoring mechanism. The anchoring locations can include openings and/or anchor elements. The barrier device can also include truss structures that provide additional strength to the barrier component. The barrier device is implantable in a patient for short term or long term applications, and can include controlled release of the therapeutic agent.

23 Claims, 10 Drawing Sheets

(56) References Cited

U.S. PATENT DOCUMENTS

| | | | |
|---|---|---|---|
| 5,171,148 A | 12/1992 | Wasserman et al. | |
| 5,176,956 A | 1/1993 | Jevne et al. | |
| 5,179,174 A | 1/1993 | Elton | |
| 5,202,310 A | 4/1993 | Levy et al. | |
| 5,254,105 A | 10/1993 | Haaga | |
| 5,356,432 A | 10/1994 | Rutkow et al. | |
| 5,368,602 A * | 11/1994 | de la Torre | 606/151 |
| 5,371,109 A | 12/1994 | Engstrom et al. | |
| 5,380,328 A | 1/1995 | Morgan | |
| 5,387,658 A | 2/1995 | Schroder et al. | |
| 5,403,283 A | 4/1995 | Luther | |
| 5,411,951 A | 5/1995 | Mitchell | |
| 5,411,988 A | 5/1995 | Bockow et al. | |
| 5,447,940 A | 9/1995 | Harvey et al. | |
| 5,464,650 A | 11/1995 | Berg et al. | |
| 5,480,653 A | 1/1996 | Aguadisch et al. | |
| 5,509,899 A | 4/1996 | Fan et al. | |
| 5,547,677 A | 8/1996 | Wright | |
| 5,549,901 A | 8/1996 | Wright | |
| 5,579,149 A | 11/1996 | Moret et al. | |
| 5,580,923 A | 12/1996 | Yeung et al. | |
| 5,589,508 A | 12/1996 | Schlotzer et al. | |
| 5,591,230 A | 1/1997 | Horn et al. | |
| 5,593,441 A | 1/1997 | Lichtenstein et al. | |
| 5,612,074 A | 3/1997 | Leach | |
| 5,614,284 A | 3/1997 | Kranzler et al. | |
| 5,627,077 A | 5/1997 | Dyllick-Brenzinger et al. | |
| 5,629,021 A | 5/1997 | Wright | |
| 5,637,113 A | 6/1997 | Tartaglia et al. | |
| 5,665,115 A | 9/1997 | Cragg | |
| 5,695,525 A * | 12/1997 | Mulhauser et al. | 606/151 |
| 5,700,286 A | 12/1997 | Tartaglia et al. | |
| 5,731,346 A | 3/1998 | Egberg et al. | |
| 5,736,152 A | 4/1998 | Dunn et al. | |
| 5,747,533 A | 5/1998 | Egberg et al. | |
| 5,753,259 A | 5/1998 | Engstrom et al. | |
| 5,760,081 A | 6/1998 | Leaf et al. | |
| 5,766,246 A | 6/1998 | Mulhauser et al. | |
| 5,766,710 A | 6/1998 | Turlund et al. | |
| 5,789,465 A | 8/1998 | Harvey et al. | |
| 5,817,343 A | 10/1998 | Burke | |
| 5,824,082 A * | 10/1998 | Brown | 623/11.11 |
| 5,837,313 A | 11/1998 | Ding et al. | |
| 5,843,919 A | 12/1998 | Burger | |
| 5,874,470 A | 2/1999 | Nehne et al. | |
| 5,879,359 A | 3/1999 | Dorigatti et al. | |
| 5,898,040 A | 4/1999 | Shalaby et al. | |
| 5,906,831 A | 5/1999 | Larsson et al. | |
| 5,931,165 A | 8/1999 | Reich et al. | |
| 5,955,502 A | 9/1999 | Hansen et al. | |
| 5,986,043 A | 11/1999 | Hubbell et al. | |
| 6,005,004 A | 12/1999 | Katz et al. | |
| 6,010,766 A | 1/2000 | Braun et al. | |
| 6,010,776 A | 1/2000 | Exsted et al. | |
| 6,015,844 A | 1/2000 | Harvey et al. | |
| 6,028,164 A | 2/2000 | Loomis | |
| 6,040,330 A | 3/2000 | Hausheer et al. | |
| 6,048,725 A | 4/2000 | Shimada et al. | |
| 6,056,970 A | 5/2000 | Greenwalt et al. | |
| 6,077,698 A | 6/2000 | Swan et al. | |
| 6,080,442 A | 6/2000 | Yoshikawa et al. | |
| 6,083,950 A | 7/2000 | Anand et al. | |
| 6,090,809 A | 7/2000 | Anand et al. | |
| 6,093,792 A | 7/2000 | Gross et al. | |
| 6,117,911 A | 9/2000 | Grainger et al. | |
| 6,120,539 A | 9/2000 | Eldridge et al. | |
| 6,120,789 A | 9/2000 | Dunn | |
| 6,132,765 A | 10/2000 | DiCosmo et al. | |
| 6,146,358 A | 11/2000 | Rowe | |
| 6,152,944 A | 11/2000 | Holman et al. | |
| 6,176,863 B1 * | 1/2001 | Kugel et al. | 606/151 |
| 6,193,746 B1 | 2/2001 | Strecker | |
| 6,197,357 B1 | 3/2001 | Lawton et al. | |
| 6,203,551 B1 | 3/2001 | Wu | |
| 6,206,916 B1 | 3/2001 | Furst | |
| 6,211,315 B1 | 4/2001 | Larock et al. | |
| 6,228,383 B1 | 5/2001 | Hansen et al. | |
| 6,229,032 B1 | 5/2001 | Jacobs et al. | |
| 6,245,366 B1 | 6/2001 | Popplewell et al. | |
| 6,245,811 B1 | 6/2001 | Horrobin et al. | |
| 6,254,634 B1 | 7/2001 | Anderson et al. | |
| 6,262,109 B1 | 7/2001 | Clark et al. | |
| 6,273,913 B1 | 8/2001 | Wright et al. | |
| 6,284,268 B1 | 9/2001 | Mishra et al. | |
| 6,299,604 B1 | 10/2001 | Ragheb et al. | |
| 6,326,360 B1 | 12/2001 | Kanazawa et al. | |
| 6,331,568 B1 | 12/2001 | Horrobin | |
| 6,342,254 B1 | 1/2002 | Soudant et al. | |
| 6,346,110 B2 | 2/2002 | Wu | |
| 6,358,556 B1 | 3/2002 | Ding et al. | |
| 6,364,893 B1 | 4/2002 | Sahatjian et al. | |
| 6,368,658 B1 | 4/2002 | Schwarz et al. | |
| 6,369,039 B1 | 4/2002 | Palasis et al. | |
| 6,387,379 B1 | 5/2002 | Goldberg et al. | |
| 6,410,587 B1 | 6/2002 | Grainger et al. | |
| 6,444,318 B1 | 9/2002 | Guire et al. | |
| 6,451,373 B1 | 9/2002 | Hossainy et al. | |
| 6,465,525 B1 | 10/2002 | Guire et al. | |
| 6,471,980 B2 | 10/2002 | Sirhan et al. | |
| 6,479,683 B1 | 11/2002 | Abney et al. | |
| 6,485,752 B1 | 11/2002 | Rein et al. | |
| 6,491,938 B2 | 12/2002 | Kunz | |
| 6,500,453 B2 | 12/2002 | Brey et al. | |
| 6,503,556 B2 | 1/2003 | Harish et al. | |
| 6,525,145 B2 | 2/2003 | Gevaert et al. | |
| 6,527,801 B1 | 3/2003 | Dutta | |
| 6,534,693 B2 | 3/2003 | Fischell et al. | |
| 6,548,081 B2 | 4/2003 | Sadozai et al. | |
| 6,565,659 B1 | 5/2003 | Pacetti et al. | |
| 6,569,441 B2 | 5/2003 | Kunz et al. | |
| 6,599,323 B2 | 7/2003 | Melican et al. | |
| 6,610,035 B2 | 8/2003 | Yang et al. | |
| 6,610,068 B1 | 8/2003 | Yang et al. | |
| 6,630,151 B1 | 10/2003 | Tarletsky et al. | |
| 6,630,167 B2 * | 10/2003 | Zhang | 424/484 |
| 6,632,822 B1 | 10/2003 | Rickards et al. | |
| 6,641,611 B2 | 11/2003 | Jayaraman | |
| 6,645,547 B1 | 11/2003 | Shekalim | |
| 6,663,880 B1 | 12/2003 | Roorda et al. | |
| 6,669,735 B1 * | 12/2003 | Pelissier | 623/23.74 |
| 6,670,355 B2 | 12/2003 | Azrolan et al. | |
| 6,677,342 B2 | 1/2004 | Wolff et al. | |
| 6,677,386 B1 | 1/2004 | Giezen et al. | |
| 6,685,956 B2 | 2/2004 | Chu et al. | |
| 6,696,583 B2 | 2/2004 | Koncar et al. | |
| 6,730,064 B2 | 5/2004 | Ragheb et al. | |
| 6,753,071 B1 | 6/2004 | Pacetti | |
| 6,761,903 B2 | 7/2004 | Chen et al. | |
| 6,764,509 B2 | 7/2004 | Chinn et al. | |
| 6,776,796 B2 | 8/2004 | Falotico et al. | |
| 6,794,485 B2 | 9/2004 | Shalaby et al. | |
| 6,833,004 B2 | 12/2004 | Ishii et al. | |
| 6,852,330 B2 | 2/2005 | Bowman et al. | |
| 6,875,230 B1 | 4/2005 | Morita et al. | |
| 6,884,428 B2 | 4/2005 | Binette et al. | |
| 6,887,270 B2 | 5/2005 | Miller et al. | |
| 6,899,729 B1 | 5/2005 | Cox et al. | |
| 6,918,927 B2 | 7/2005 | Bates et al. | |
| 6,996,952 B2 | 2/2006 | Gupta et al. | |
| 7,070,858 B2 | 7/2006 | Shalaby et al. | |
| 7,101,381 B2 | 9/2006 | Ford et al. | |
| 7,152,611 B2 | 12/2006 | Brown et al. | |
| 7,323,189 B2 | 1/2008 | Pathak | |
| 7,415,811 B2 | 8/2008 | Gottlieb et al. | |
| 7,854,958 B2 | 12/2010 | Kramer | |
| 8,124,127 B2 | 2/2012 | Faucher et al. | |
| 8,263,102 B2 | 9/2012 | Labrecque et al. | |
| 8,308,684 B2 | 11/2012 | Herweck et al. | |
| 8,367,099 B2 | 2/2013 | Herweck et al. | |
| 8,501,229 B2 | 8/2013 | Faucher et al. | |
| 8,722,077 B2 | 5/2014 | Labrecque et al. | |
| 9,000,040 B2 | 4/2015 | Faucher et al. | |
| 9,012,506 B2 | 4/2015 | Faucher et al. | |
| 2001/0025034 A1 | 9/2001 | Arbiser | |

(56) References Cited

U.S. PATENT DOCUMENTS

| | | |
|---|---|---|
| 2001/0025196 A1 | 9/2001 | Chinn et al. |
| 2001/0051595 A1 | 12/2001 | Lyons et al. |
| 2002/0002154 A1 | 1/2002 | Guivarch et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0117007 A1 | 6/2004 | Whitbourne et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0124062 A1 | 6/2005 | Subirade |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0051544 A1 * | 3/2006 | Goldmann ................ 428/35.8 |
| 2006/0058881 A1 | 3/2006 | Trieu |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 * | 3/2006 | Swanick et al. ............. 424/434 |
| 2006/0068674 A1 | 3/2006 | Dixit et al. |
| 2006/0078586 A1 * | 4/2006 | Ferraro et al. ............... 424/423 |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0092665 A1 | 4/2009 | Mitra et al. |
| 2009/0181074 A1 | 7/2009 | Makower et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0045050 A1 | 2/2011 | Elbayoumi et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | | |
|---|---|---|---|
| EP | 610731 A1 * | 8/1994 | ............. A61L 31/00 |
| EP | 0623354 | 11/1994 | |

(56) References Cited

FOREIGN PATENT DOCUMENTS

| | | |
|---|---|---|
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 A1 | 1/2003 |
| EP | 1364628 | 11/2003 |
| EP | 1520795 | 4/2005 |
| EP | 1557183 | 7/2005 |
| EP | 2083875 | 8/2009 |
| EP | 1 402 906 | 6/2011 |
| KR | 20080025986 | 3/2008 |
| WO | WO 86/00912 | 2/1986 |
| WO | WO 90/01969 | 3/1990 |
| WO | 90/08544 A1 | 8/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | 98/46287 A2 | 10/1998 |
| WO | WO 98/54275 | 12/1998 |
| WO | WO 99/25336 | 5/1999 |
| WO | WO 00/40278 A1 | 7/2000 |
| WO | WO 00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO 02/100455 | 12/2002 |
| WO | WO 03/000308 A1 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO 03/041756 | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2004101010 A1 * | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | 2005/082434 A2 | 9/2005 |
| WO | WO 2005082434 A2 * | 9/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | 2008/010788 A2 | 1/2008 |
| WO | 2008/016664 A2 | 2/2008 |
| WO | 2008/057328 A2 | 5/2008 |
| WO | WO 2008/057328 | 5/2008 |
| WO | 2010/042134 A1 | 4/2010 |
| WO | 2010/042241 A1 | 4/2010 |
| WO | WO 2012/009707 | 1/2012 |

OTHER PUBLICATIONS

Wexler et al. Chemical Reviews 1964 64(6):591-611.*
Polymer—The Chambers 21st Century Dictionary M. Robinson and G. Davidson (Eds.), London, United Kingdom: Chambers Harrap. Retrieved from http://search.credoreference.com/content/entry/chambdict/polymer/0.*
Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst/polymer/0.*
Falagas et al. European Society of Clinical Microbiology and Infection Diseases 2005 11:3-8.*
Bimbo (INFORM 1998 9(5):473-483.*
Ahuja et al., "Prevention of Postoperative Intraperitoneal Adhesions—An Experimental Study in Rats," Journal of Indian Pediatric Surgery. 7:15-20(2002).
Cure in Academic Press Dictionary of Science and Technology (1992).
Autosuture, "Parietex™ Composite OS Series MESH" Retrieved online at http://www.autosuture.com/AutoSuture/pagebuilder.aspx?topicID=135734&breadcrumbs=135601:0 (2007).
Rutkow, Ira M. et al., "Tension-free inguinal herniorrhaphy: A preliminary report on the 'mesh plug' technique," Surgery. 114:3-8(1993).
"Polymerization" Merriam-Webster Online Dictionary, retrieved from <www.merriam-webster.com> on Dec. 13, 2009; Merriam-Webster's Inc. 2009; pp. 1.
Drummond, Calum J., et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. (Some empirical equations for oxopolymerization of linseed oil. Progress in Organic Coatings 2004, vol. 51, 365-371).
Hwang, Chao-Wei et al, "Physiological Transport Forces Govern Drug Distribution for Stent-Based Delivery," Circulation, vol. 104:600-605 (2001).
Jonasson, Lena, et al., "Cyclosporon A inhibits smooth muscle proliferation in the vascular response to injury," Proc. Natl. Acad. Sci. USA, vol. 85: 2303-2306 (1988).
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).
Ogunniyi, D.S., "Castor oil: A vital industrial raw material," Biosource Technology, vol. 97:1086-1091 (2006).
Redman, L.V., et al., "The drying rate of raw paint oils—a comparison," The Journal of Industrial and Engineering Chemistry, vol. 5: 630-636 (1913).
Salu, Koen J. et al, "Addition of cytochalasin D to a biocompatible oil stent coating inhibits intimal hyperplasia in a porcine coronary model," Coronary Artery Disease, vol. 14(8):545-555 (2003).
Scheller, Bruno et al, "Addition of Paclitaxel to Contrast Media Prevents Restenosis After Coronary Stent Implantation," Journal of the American College of Cardiology, vol. 42(8):1415-1420 (2003).
Shahidi, Fereidoon ed.; "Bailey's Industrial Oil and Fats Products" 2005; John Wiley and Sons; vol. 5, Edible Oil and Fat Products: Processing Technologies, pp. 1-15.
Van der Giessen, Willem J. et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
Binder et al., "Chromatographic Analysis of Seed Oils. Fatty Acid Composition of Castor Oil," The Journal of the American Oil Chemists' Society, vol. 39:513-517 (1962).
CECW-EE, "Ch. 4: Coating Types and Characteristics," Engineering and Design—Painting: New Construction and Maintenance, pp. 4-1 to 4-24 (1995).
Wikipedia, "Sirolimus," pp. 1-13, available online at http://en.wikipedia.org/wiki/Sirolimus, date accessed May 11, 2011.
PCT/US05/034601, Apr. 10, 2006, International Search Report.
PCT/US05/034610, Mar. 16, 2006, International Search Report.

(56) References Cited

OTHER PUBLICATIONS

PCT/US05/034614, Aug. 29, 2006, International Search Report.
PCT/US05/034615, May 16, 2006, International Search Report.
PCT/US05/034678, Aug. 28, 2006, International Search Report.
PCT/US05/034681, Jul. 26, 2006, International Search Report.
PCT/US05/034682, Jul. 20, 2006, International Search Report.
PCT/US05/034836, Jul. 6, 2006, International Search Report.
PCT/US05/034941, May 4, 2006, International Search Report.
PCT/US06/037184, Feb. 22, 2007, International Search Report.
PCT/US06/040753, Sep. 9, 2008, International Preliminary Report on Patentability.
PCT/US06/040753, Sep. 24, 2007, International Search Report.
PCT/US07/019978, May 7, 2009, International Search Report.
PCT/US07/022860, Apr. 22, 2009, International Search Report.
PCT/US07/022944, Apr. 8, 2009, International Search Report.
PCT/US08/000565, May 4, 2009, International Search Report.
PCT/US08/071547, Aug. 26, 2010, International Preliminary Examination Report.
PCT/US08/071547, Oct. 22, 2008, International Search Report.
PCT/US08/071565, Aug. 27, 2009, International Preliminary Report on Patentability.
PCT/US08/071565, Nov. 10, 2008, International Search Report.
PCT/US08/085386, Feb. 4, 2009, International Search Report.
PCT/US09/037364, Aug. 27, 2009, International Search Report.
PCT/US10/026521, Jun. 23, 2010, International Search Report.
PCT/US10/052899, Jan. 10, 2011, International Search Report.
U.S. Appl. No. 11/236,908, May 17, 2011, Non-final.
U.S. Appl. No. 11/236,908, Mar. 25, 2006, Non-final.
U.S. Appl. No. 11/236,908, Aug. 24, 2009, Final.
U.S. Appl. No. 11/236,943, Dec. 23, 2009, Final.
U.S. Appl. No. 11/236,943, Mar. 5, 2009, Non-final.
U.S. Appl. No. 11/236,977, Aug. 3, 2009, Non-final.
U.S. Appl. No. 11/237,263, Jul. 7, 2010, Final.
U.S. Appl. No. 11/237,263, Oct. 7, 2009, Non-final.
U.S. Appl. No. 11/237,264, Jun. 2, 2010, Final.
U.S. Appl. No. 11/237,264, Oct. 5, 2009, Non-final.
U.S. Appl. No. 11/237,264, Nov. 23, 2010, Final.
U.S. Appl. No. 11/237,420, Mar. 5, 2009, Non-final.
U.S. Appl. No. 11/237,420, Nov. 4, 2009, Final.
U.S. Appl. No. 11/237,420, Dec. 6, 2010, Non-final.
U.S. Appl. No. 11/238,532, Mar. 30, 2009, Non-final.
U.S. Appl. No. 11/238,532, Sep. 9, 2009, Final.
U.S. Appl. No. 11/238,554, May 12, 2010, Final.
U.S. Appl. No. 11/238,554, Oct. 9, 2009, Non-final.
U.S. Appl. No. 11/238,554, May 1, 2009, Final.
U.S. Appl. No. 11/238,554, Jul. 25, 2008, Non-final.
U.S. Appl. No. 11/238,564, Apr. 16, 2008, Non-final.
U.S. Appl. No. 11/238,564, Aug. 6, 2009, Final.
U.S. Appl. No. 11/239,555, Mar. 30, 2009, Non-final.
U.S. Appl. No. 11/525,328, Apr. 30, 2007, Non-final.
U.S. Appl. No. 11/525,390, Jul. 14, 2010, Non-final.
U.S. Appl. No. 11/525,390, Feb. 21, 2011, Final.
U.S. Appl. No. 11/582,135, May 12, 2011, Final.
U.S. Appl. No. 11/582,135, Nov. 9, 2010, Non-Final.
U.S. Appl. No. 11/582,135, Jan. 6, 2010, Non-final.
U.S. Appl. No. 11/582,135, May 12, 2009, Non-final.
U.S. Appl. No. 11/701,799, Apr. 12, 2010, Non-final.
U.S. Appl. No. 11/978,840, Dec. 3, 2010, Non-final.
U.S. Appl. No. 11/980,155, Mar. 24, 2011, Non-final.
U.S. Appl. No. 12/325,546, Feb. 25, 2010, Non-final.
U.S. Appl. No. 12/325,546, Aug. 31, 2010, Final.
U.S. Appl. No. 12/364,763, Dec. 11, 2009, Non-final.
U.S. Appl. No. 12/364,763, Sep. 21, 2010, Final.
U.S. Appl. No. 11/236,908, May 5, 2009.
U.S. Appl. No. 11/236,908, Dec. 2, 2010.
U.S. Appl. No. 11/237,420, May 5, 2009.
U.S. Appl. No. 11/582,135, Dec. 7, 2010.
U.S. Appl. No. 12/325,546, Dec. 2, 2010.
U.S. Appl. No. 12/364,763, Dec. 2, 2010.

Supplementary European Search Report for Application No. EP 08877338.7, dated Aug. 16, 2012.
Supplementary European Search Report for Application No. EP09819594.4, dated Aug. 14, 2012.
Final Office Action for U.S. Appl. No. 12/182,261 mailed Apr. 30, 2012.
Notice of Allowance for U.S. Appl. No. 11/236,908, mailed May 11, 2012.
Final Office Action for U.S. Appl. No. 12/401,243, mailed Jun. 11, 2012.
Notice of Allowance for U.S. Appl. No. 12/182,261, mailed Jul. 23, 2012.
Advisory Action for U.S. Appl. No. 12/401,243, mailed Aug. 27, 2012.
Final Office Action for U.S. Appl. No. 12/581,582 mailed Aug. 29, 2012.
Final Office Action for U.S. Appl. No. 11/701,799, mailed Feb. 13, 2012.
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Supplementary European Search Report in Application No. EP 05 80 4291, dated Jul. 26, 2011.
Supplementary European Search Report for Application No. EP 05 80 289, dated Jul. 27, 2011.
Supplementary European Search Report in Application No. EP 05 85 8430, dated Aug. 18, 2011.
Supplementary European Search Report in Application No. 05 800 844, dated Aug. 19, 2011.
Non-final Office Action for U.S. Appl. No. 11/525,390, mailed Jul. 11, 2011.
Final Office Action for U.S. Appl. No. 11/237,420, mailed Jul. 13, 2011.
Non-Final Office Action for U.S. Appl. No. 11/582,135, mailed Oct. 14, 2011.
Final Office Action for U.S. Appl. No. 11/980,155, mailed Oct. 21, 2011.
Non-Final Office Action for U.S. Appl. No. 11/236,908, mailed Dec. 2, 2011.
Non-Final Office Action for U.S. Appl. No. 12/182,261, mailed Dec. 21, 2011.
Non-Final Office Action for U.S. Appl. No. 12/401,243, mailed Jan. 5, 2012.
Notice of Allowance for U.S. Appl. No. 11/582,135, mailed Jan. 9, 2012.
Non-Final Office Action for U.S. Appl. No. 12/182,165, mailed Jan. 5, 2012.
Final Office Action for U.S. Appl. No. 11/978,840, mailed Jun. 22, 2011.
Final Office Action for U.S. Appl. No. 11/701,799, mailed Nov. 23, 2010.
Non-Final Office Action for U.S. Appl. No. 11/701,799, mailed Aug. 17, 2011.
Ackman, R.G "Fish Oils", *Bailey's Industrial Oil and Fat Products*, 6th Edition, 279-317 (2005).
Andes, et al. "Antiproliferative Strategies for the Treatment of Vascular Proliferative Disease", *Current Vascular Pharmacology*, 1)1): 85-98 (2003).
Jorge, N., "Grasas y Aceites", 48(1): 17-24, (1997).
Lipids, Chapter 19, pp. 1-12 (2002).
Winter, et al., "Physical and Chemical Gelation" *Encyclopedia of Materials—Science and Technology*, vols. 1-11: 6691-6999 2001.
International Search Report for PCT/US2011/44292, dated Dec. 6, 2011.
Supplementary European Search Report for Application No. EP 12004057, dated Apr. 10, 2013.
Notice of Allowance for U.S. Appl. No. 11/525,390, mailed Oct. 4, 2012.
Advisory Action for U.S. Appl. No. 12/581,582, dated Nov. 14, 2012.

(56) References Cited

OTHER PUBLICATIONS

Notice of Allowance for U.S. Appl. No. 11/525,390, dated Nov. 20, 2012.
Notice of Allowance for U.S. Appl. No. 11/525,390, mailed Nov. 30, 2012.
Non-Final Office Action for U.S. Appl. No. 13/404,487, dated Dec. 20, 2012.
Non-Final Office Action for U.S. Appl. No. 13/184,512, dated Jan. 31, 2013.
Non-Final Office Action for U.S. Appl. No. 11/978,840, dated Feb. 19, 2013.
Non-Final Office Action for U.S. Appl. No. 13/682,991, dated Mar. 18, 2013.
Notice of Allowance for U.S. Appl. No. 13/404,487, dated Apr. 2, 2013.
Non-Final Office Action for U.S. Appl. No. 11/236,943, dated Apr. 22, 2013.
Final Office Action for U.S. Appl. No. 13/184,512, date Jun. 25, 2013.
Non-Final Office Action for U.S. Appl. No. 11/237,264, dated Jul. 3, 2013.
Non-Final Office Action for U.S. Appl. No. 13/593,656, dated Jul. 15, 2013.
Notice of Allowance for U.S. Appl. No. 13/682,991, dated Aug. 1, 2013.
Notice of Allowance for U.S. Appl. No. 11/978,840, dated Aug. 6, 2013.
Non-Final Office Action for U.S. Appl. No. 12/581,582 mailed Mar. 14, 2012.
Final Office Action for U.S. Appl. No. 12/185,165 mailed Apr. 6, 2012.
Mallegol, "Long-Term Behavior of Oil-Based Varnishes and Paints Photo- and Thermooxidation of Cured Linseed Oil", *Journal of the American Oil Chemists' Society*, 77:257-263 (2000).
International Search Report for International Application PCT/US2013/044653, dated Sep. 4, 2013.
Supplementary European Search Report for Application No. EP 10825447, dated Mar. 31, 2014.
Non-Final Office Action for U.S. Appl. No. 11/237,420, dated Nov. 12, 2013.
Non-Final Office Action for U.S. Appl. No. 11/980,155, dated Nov. 12, 2013.
Final Office Action for U.S. Appl. No. 11/236,943, dated Dec. 4, 2013.
Final Office Action for U.S. Appl. No. 11/237,264, dated Dec. 17, 2013.
Notice of Allowance for U.S. Appl. No. 13/593,656, dated Jan. 24, 2014.
Notice of Allowance for U.S. Appl. No. 11/237,264, dated Mar. 27, 2014.
Notice of Allowance for U.S. Appl. No. 11/237,263, dated Mar. 27, 2014.
Non Final Office Action for U.S. Appl. No. 12/325,546, dated Apr. 22, 2014.
Non Final Office Action for U.S. Appl. No. 12/364,763, dated Apr. 23, 2014.
Non Final Office Action for U.S. Appl. No. 12/401,243, mailed May 8, 2014.
Non Final Office Action for U.S. Appl. No. 12/581,582, dated May 29, 2014.
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47; 2157-2161 (2005).
Sano, et al., "A controlled Trial of Selegiline, Alpha-Tocopherol, or Both as Treatment for Alzheimer's Disease", *The New England Journal of Medicine*, 336; 1216-1222 (1997).
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Non-Final Office Action for U.S. Appl. No. 11/701,799, dated Jul. 22, 2014.
Final Office Action for U.S. Appl. No. 11/701,799, dated Mar. 12, 2015.
Lead, Article from Center for Disease Control & Prevention (CDC), Nov. 2009, http://www.cdc.gov/biomonitoring/pdf/Lead_FactSheet.pdf, 2 pages.
Final Office Action for U.S. Appl. No. 13/843,068, dated Apr. 23, 2015.
Final Office Action for U.S. Appl. No. 13/184,512, dated Apr. 28, 2015.
Wikipedia, Sunflower oil, https://en.wikipedia.org/wiki/Sunflower_oil, accessed Jul. 23, 2015 in related U.S. Appl. No. 14/252,671, pp. 1-7.
Esoteric Oils, Peppermint essential oil information, http://www.essentialoils.co.za/essential-oils/peppermint.htm, accessed Jul. 23, 2015 in related U.S. Appl. No. 14/252,671, pp. 1-7.
Orthomolecular, Fish Oil, Jun. 29, 2004, http://orthomolecular.org/nutrients/fishoil.html, accessed Jul. 22, 2015 in related U.S. Appl. No. 14/252,671, p. 1.
Non-Final Office Action for U.S. Appl. No. 13/843,068, dated Sep. 29, 2014.
Notice of Allowance for U.S. Appl. No. 11/236,943, dated Oct. 6, 2014.
Non-Final Office Action for U.S. Appl. No. 13/184,512, dated Oct. 10, 2014.
Non-Final Office Action for U.S. Appl. No. 11/980,155, dated Nov. 7, 2014.
Notice of Allowance for U.S. Appl. No. 12/364,763, dated Dec. 5, 2014.
Notice of Allowance for U.S. Appl. No. 12/325,546, dated Dec. 8, 2014.
Final Office Action for U.S. Appl. No. 12/581,582, dated Jan. 8, 2015.
Final Office Action for U.S. Appl. No. 12/401,243, dated Jan. 16, 2015.
Non-Final Office Action for U.S. Appl. No. 11/237,420, dated Jan. 21, 2015.
Notice of Allowance for U.S. Appl. No. 13/943,489, mailed Jan. 29, 2015.
Lewis, Richard J., Sr., Hawley's Condensed Chemical Dictionary (2001), 308, 309 and 896-898, Fourteenth Edition, John Wiley & Sons, Inc., New York.
Fineberg, H. and Johanson, A.G., Industrial Use of Fish Oils, http://spo.nmfs.noaa.gov/Circulars/CIRC278.pdf (downloaded Aug. 3, 2015).
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20NAC%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
Fats & Oils (2008) at http://scifun.chem.wisc.edu/chemweek/pdf/fats&oils.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).

(56) References Cited

OTHER PUBLICATIONS

Hortolam, Juliane G., et al., "Connective tissue diseases following silicone breast implantation: where do we stand?", Clinics, 2013, vol. 3, p. 281.
Lidar, M. et al., "Silicone and sclerodema revisited", Lupus, 2012, vol. 21, pp. 121-127.
Swanson, Danielle, et al., Omega-3 Fatty Acids EPA and DHA: Health Benefits Throughout Life, 3 Advances in Nutrition 1-7 (American Society for Nutrition 2012).
SepraFilm Adhesion Barrier package insert (Genzyme Biosurgery 2008).
Sannino, Alessandro, et al., Biodegradeable Cellulose-based Hydrogels: Design and Applications, 2 Materials, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.
Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, Vet. Med.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Flub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm?Id=9&sub=20&cont=522 (downloaded Nov. 10, 2015).
Refined soybean oil not an allergen, say food scientists, FOOD navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinic.org/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:iessionid=33N2RBQDVODZKCQPCCEGU3AKB2IIWTT1 (2006).
Orthovisc, "What is Orthovisc®?" retrieved online at http://www.orthovisc.com/xhtmlbgdisplay.jhtml?temname=about_orthovisc (2005).
Orthovisc, "Your Knees and Osteoarthritis", retrieved online at http://www.orthovisc.com/xhtmlbgdisplay.jhtml?temname=understanding_knee_oa (2003).
Orthovisc, "What to expect from your treatment," retrieved online at http://www.orthovisc.com/xhtmlbgdisplay.jhtml?temname=what_to_expect (2007).
Orthovisc, "Tools and Resources for Managing Your Osteoarthritis", retrieved online at http://www.orthovisc.com/xhtmlbgdisplay.jhtml?itemname=patient_resources (2007).
Pohibinska, A., et al., "Time to reconsider saline as the ideal rinsing solution during abdominal surgery", The American Journal of Surgery, vol. 192, pp. 281-222 (2007).
Singh, Alok, et al., "Facilitated Stent Delivery Using Applied Topical Lubrication", Catherization and Cardiovascular Interventions, vol. 69, pp. 218-222 (2007).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (!987).
Triglycerides, https://www.lipid.org/sites/default/files/triglycerides.pdf (downloaded Sep. 24, 2015).
F.D. Gunstone, Fatty Acid and Lipid Chemistry, pp. 69 and 72, Aspen Publishers, Inc., Gaithersburg, Maryland, 1999.
Final Office Action dated Mar. 30, 2017 for related U.S. Appl. No. 11/237,420, 20 pages.
Henderson, R. James et al., "Hydrolysis of Fish Oils Containing Polymers of Triacylglycerols by Pancreatic Lipase in vitro", LIPIDS, vol. 28, No. 4, 1993, pp. 313-319.

\* cited by examiner

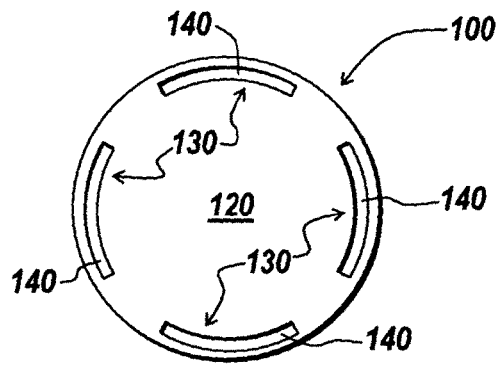
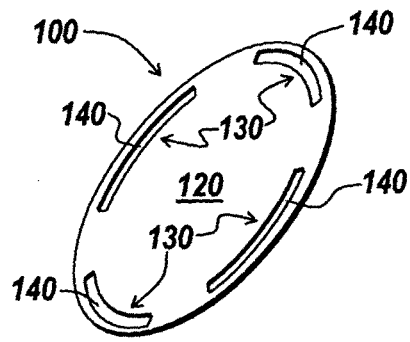
Fig. 3A                Fig. 3B
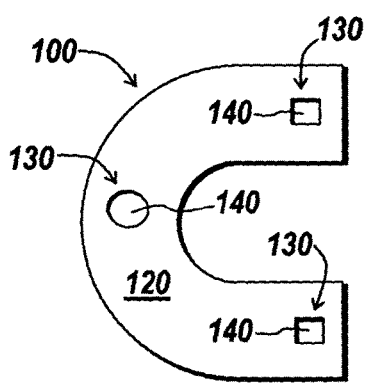
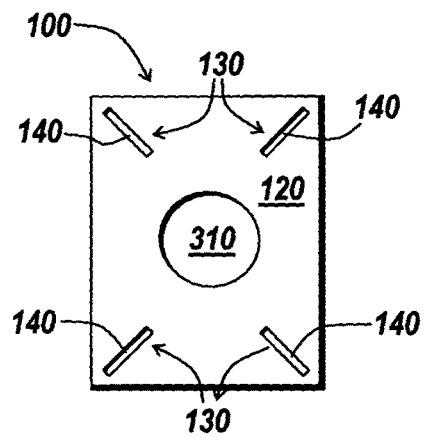
Fig. 3C                Fig. 3D
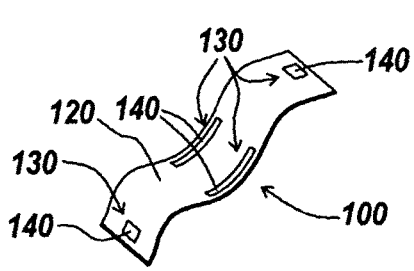
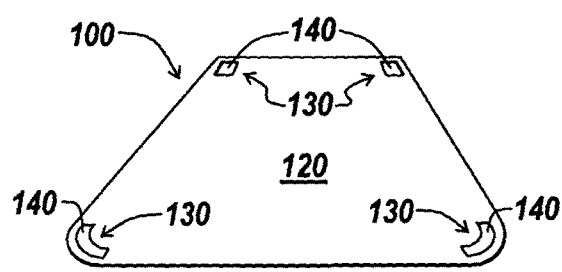
Fig. 3E                Fig. 3F

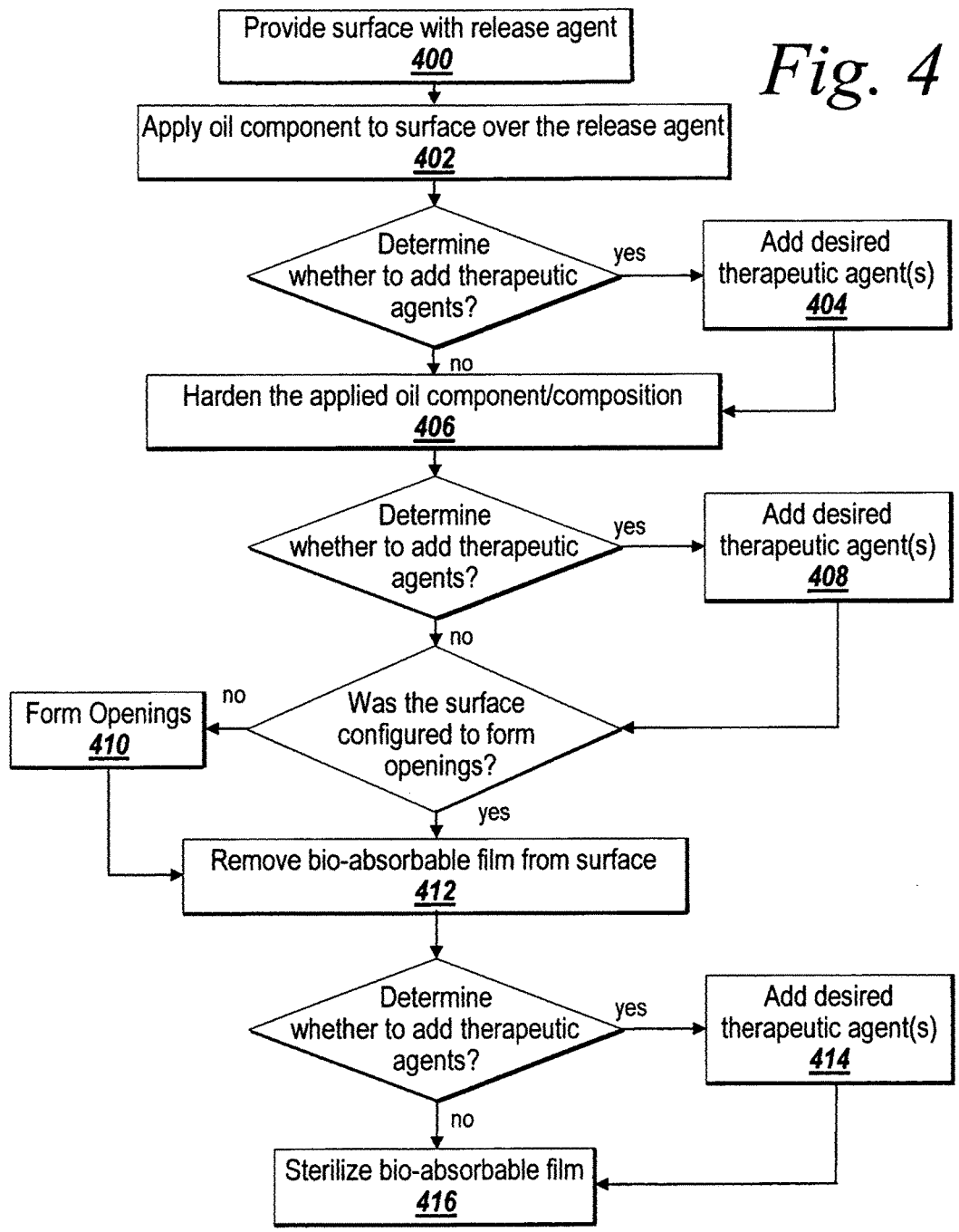

US 9,801,982 B2

IMPLANTABLE BARRIER DEVICE

CROSS-REFERENCE TO RELATED APPLICATIONS

This application is a continuation-in-part, and claims priority to U.S. application Ser. No. 11/237,420, filed on Sep. 28, 2005, which claims the benefit of U.S. Provisional Application Ser. No. 60/613,808, filed on Sep. 28, 2004. This application is also a continuation-in-part, and claims priority to U.S. application Ser. No. 11/980,155, filed Oct. 30, 2007 which claims the benefit of U.S. Provisional Application Ser. No. 60/856,983, filed on Nov. 6, 2006. This application also claims the benefit of said applications for all subject matter in common with this application. The disclosure of said applications is hereby incorporated by reference in its entirety.

FIELD OF THE INVENTION

The present invention relates to implantable devices and more particularly to a soft tissue device having one or more anchoring locations to assist in anchoring the implantable device to a target area.

BACKGROUND OF THE INVENTION

Biocompatible medical films are most often used in surgical settings as a physical barrier to help separate certain organs from adjacent tissues and medical devices following surgical intervention or blunt dissection to minimize adhesion formation between adjacent tissues. For example, SEPRAFILM®, a product of Genzyme Corporation of Cambridge, Mass., is used in patients undergoing either open or laparoscopic abdominal or pelvic surgeries as an implantable treatment intended to reduce the incidence, extent, and severity of postoperative adhesion formation between different tissues and organs and implantable medical devices, such as soft tissue support membranes and mesh, or combinations of non-absorbable films and meshes.

U.S. Pat. No. 5,017,229 (the "'229 patent") is directed to a water insoluble, biocompatible gel that includes the reaction product of hyaluronic acid, a polyanionic polysaccharide, and an activating agent. The gel described in the '229 patent can be provided in the form of a tissue to tissue adhesion prevention composition, such as a membrane or composition suitable for incorporation into a syringe. The gel is described as being able to form a film by being cast into a sheet form, extruded, compressed, or allowed to dehydrate in a flat sheet. When modified with polysaccharide, the biodegradable film forms the above-described SEPRAFILM® adhesion-limiting or adhesion barrier product made commercially available as a dehydrated bio-dissolvable single layer sheet.

Many commercially available tissue to tissue adhesion prevention and adhesion barrier film products often can be difficult to handle and apply to the targeted location due to their chemical make up and rapid bio-dissolvable properties. The composition and limited structural strength properties of these bio-dissolvable products result in the material forming the products softening relatively quickly upon exposure to fluids; thus, handling of these barrier film products can be difficult during most open and laparoscopic surgical intervention operations. In addition, many of these films become tacky when exposed to fluid and adhere to an implanted location. When these barrier films break down, they remain in place due to their adhesive properties.

There are, however, commercially available barrier films which do not exhibit adhesive properties when exposed to fluid, and therefore do not stick to the implanted location. In some instances, these films can shift and can bunch or ball up; thereby reducing the effectiveness of these films. For example, after spinal surgery the film can be placed between the spine and soft tissue surrounding the spine to prevent the soft tissue from growing into the spine. If the film shifts to expose the spine to the soft tissue before the spinal area has substantially healed the soft tissue can grow into the spine.

While barrier films can be formed on reinforced devices, such as surgical meshes, to provide additional structure to the barrier films, there may be some instances where the use of an underlying mesh is undesirable. For example, in some instances it may be desirable simply to have a barrier between connective tissues and/or bones to prevent adjacent connective tissues from growing together without providing the additional structure of an underlying mesh.

SUMMARY

There is a need for an anti-adhesive tissue separating implantable barrier device (i.e., a barrier device that does not adhere to an anatomical area or to itself) that is capable of being anchored to the soft tissue to prevent or substantially reduce the shifting while the soft tissue heals. The implantable device may have the ability to delivery therapeutic agents and may have one or more surfaces that modulate healing.

The barrier device can have one or more anchoring locations disposed on the barrier device to provide one or more areas that provide an interface for anchoring the barrier device to soft tissue. The anchoring of the implantable barrier device to the tissue via the anchoring locations can occur using an anchoring mechanism, such as adhesive, a suture, a staple, a tack, or any other anchoring or fastening devices that are commonly applied for affixing implantable devices directly to tissue. The present invention is directed toward further solutions to address this need, in addition to having other desirable characteristics.

In one aspect, a barrier device that comprises a barrier component and an anchoring location is disclosed. The barrier component is composed of a non-polymeric cross-linked gel that forms a surface. The anchoring location is formed at least one of on, in, or about the surface of the barrier component and is composed of at least one of an anchor element or an opening. The opening extends through the barrier component and the anchoring location occupies a first area that is less than an area of the barrier component.

In another aspect, a barrier device that includes a barrier component and at least one anchor element is disclosed. The barrier component is composed of a bio-absorbable and anti-adhesive film. The at least one anchor element is coupled to the barrier component and is composed of a biocompatible material. The at least one anchor element has an area that is less than the area of the barrier component to provide an anchoring location on the barrier device for anchoring the barrier device to an anatomical area.

In yet another aspect, a method of developing a barrier device is disclosed. The method includes providing an anchor element and combining the anchor element with an oil component that is not cured. The method also includes curing the oil component to form a barrier device having a barrier component that is coupled to the anchor element. The anchor element has an area that is less than the area of the barrier component.

BRIEF DESCRIPTION OF THE FIGURES

These and other characteristics of the present invention will be more fully understood by reference to the following detailed description in conjunction with the attached drawings, in which:

FIGS. 3A-F are diagrammatic views of the barrier device in accordance with another aspect of the present invention;

FIG. 4 is a flow chart illustrating a method of making the barrier device of the present invention, in accordance with one embodiment of the present invention;

DETAILED DESCRIPTION

Figure 1:
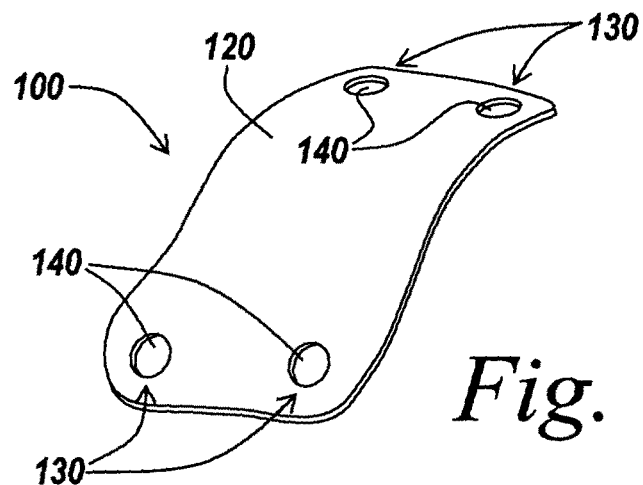
FIG. 1 a diagrammatic illustration of a barrier device realized as a standalone film, according to one embodiment of the present invention.

Exemplary embodiments provide a barrier device having a one or more barrier components and one or more anchoring locations that are disposed in, on, or about the one or more barrier components. The one or more barrier components can exhibit modulated healing properties, anti-inflammatory properties, non-inflammatory properties, therapeutic properties, and/or adhesion-limiting properties. The one or more anchoring locations can facilitate attachment of the barrier device to the soft tissue of a patient.

In some embodiments, an anchoring location can be an opening, such as a hole, slit, flap, or the like in the barrier component that provides an area (i.e., anchoring location) on the barrier device that allows the barrier device to be anchored to the soft tissue of the patient. In other embodiments, the one or more anchoring locations can include one or more anchor elements, such as a biocompatible material (e.g., a surgical mesh), to assist in the attachment of the barrier device to soft tissue of a patient. The anchor elements can provide stability, resistance to disruption or tearing at the anchoring location, and/or resistance to material separation of the barrier device from support tissue. The number, type (e.g., holes, slits, flaps, and/or anchor elements), size, and shape of the anchoring locations as well as the placement of the anchoring locations can vary and may be based on an anatomical application.

The one or more anchoring locations allow the anti-adhesive barrier device to be held in position after implantation to maintain a physical and/or biological barrier between adjacent soft tissues and/or bones. The barrier device can be implantable in a patient for short term or long term applications, and can include controlled release of the therapeutic agent.

The one or more barrier components can be generally formed of a biocompatible oil or an oil composition formed in part of a biocompatible oil (the biocompatible oil and oil composition are referred to hereinafter as the oil component). In addition, the oil component can include a therapeutic agent component, such as a drug or other bioactive agent. As implemented herein, the barrier component can be a non-polymeric cross-linked gel derived at least in part from a fatty acid compound. One or more anchoring locations can be disposed on, in, or about the barrier component to create the inventive barrier device.

In some embodiments, the barrier device can also include biocompatible reinforcing truss structures that can be disposed on, in, or about a surface of the barrier component to reinforce the barrier device. The number, shape, size, rigidity, and locations of the reinforcing truss structures can vary and may be based on the anatomical application.

There are a number of terms and phrases utilized herein. Additional clarification and confirmation of some of these terms and phrases is provided immediately below and throughout this disclosure.

The term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents or capable of being broken down by microorganisms or biological processes, in a manner that does not result in cellular uptake of the biodegradable substance. Biodegradation relates to the breaking down and distributing of a substance through the patient's body and not the consumption by or penetration into the localized cells of the patient's body tissue (i.e. bio-absorption). Biodegradable substances, such as polymers, can cause inflammatory response due to either the parent substance or those substances formed during breakdown. The parent substance and/or those substances formed during breakdown may or may not be absorbed by tissues. Bio-absorbable substances break down into substances or components that do not cause an inflammatory response and can be consumed by the cells forming the body tissues.

The phrase "controlled release" generally refers to the release of a biologically active agent in a predictable manner over a desired period of time. Controlled release includes the provision of an initial burst of release upon implantation, followed by the predictable release over the predetermined time period. Accordingly, controlled release includes such embodiments as those that release substantially all or a significant portion of the biologically active agent in a predictable manner and a substantially lesser amount of the biologically active agent for a duration thereafter. Additional embodiments include delivery of a biologically active agent to a targeted location along with the bioabsorbable gel components at the cellular level It should be noted that the phrase "cross-linked gel," as utilized herein with reference to the present invention, refers to a gel that is non-polymeric and is derived from an oil component comprising molecules covalently cross-linked into a three-dimensional network by one or more of ester, ether, peroxide, and/or carbon-carbon bonds in a substantially random configuration that can reversibly convert into oil compounds. In various preferred embodiments, the oil component comprises a fatty acid molecule, a glyceride, and combinations thereof.

Furthermore, "curing" with respect to the present invention generally refers to thickening, hardening, or drying of a material brought about by heat, UV light, chemical means, reaction with biologically active agent and/or reactive gasses.

Modulated healing can be described as the in-vivo effect observed post-implant in which the biological response is altered resulting in a significant reduction in foreign body response. As utilized herein, the phrase "modulated healing" and variants of this language generally refer to the modulation (e.g., alteration, delay, retardation, reduction, detaining) of a process involving different cascades or sequences of naturally occurring tissue repair in response to localized tissue injury, substantially reducing their inflammatory effect. Modulated healing encompasses many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other. For example, the bio-absorbable oils described herein can alter, delay, retard, reduce, and/or detain one or more of the phases associated with healing of vascular injury caused by medical procedures, including, but not limited to, the inflammatory phase (e.g., platelet or fibrin deposition), and the proliferative phase. In one embodiment, "modulated healing" refers to the ability of a non-polymeric bio-absorbable cross-linked gel to alter a substantial inflammatory phase (e.g., platelet or fibrin deposition) at the beginning of the tissue healing process. As used herein, the phrase "alter a substantial inflammatory phase" refers to the ability of the non-polymeric bio-absorbable cross-linked gel to substantially reduce the inflammatory response at an injury site. In such an instance, a minor amount of inflammation may ensue in response to tissue injury, but this level of inflammation response, e.g., platelet and/or fibrin deposition, is substantially reduced when compared to inflammation that takes place in the absence of the non-polymeric bio-absorbable cross-linked gel.

For example, the non-polymeric bio-absorbable cross-linked gel discussed herein has been shown experimentally in animal models to delay or alter the inflammatory response associated with vascular injury, as well as excessive formation of connective fibrous tissue following tissue injury. The non-polymeric bio-absorbable cross-linked gel has also been shown experimentally in animal models to delay or reduce fibrin deposition and platelet attachment to a blood contact surface following vascular injury. Additionally, experiments have shown that the non-polymeric bio-absorbable cross-linked gel has resulted in a less dense, but uniformly confluent cellular overgrowth of a porous implanted mesh structure with little to no fibrous capsule formation.

Accordingly, the non-polymeric bio-absorbable cross-linked gel discussed herein provides an excellent absorbable cellular interface suitable for use with a surgical instrument or a medical device and results in a modulated healing effect. The non-polymeric bio-absorbable cross-linked gel generally limits or avoids the generation of scar tissue and promotes the formation of healthy tissue at a modulated or delayed period in time following the injury. Without being bound by theory, this modulated healing effect can be attributed to the modulation (e.g., alteration, delay, retardation, reduction, detaining) of any of the molecular processes associated with the healing processes of vascular injury. For example, the non-polymeric bio-absorbable cross-linked gel can act as a barrier or blocking layer between adjacent soft tissue with vessel walls where cells (e.g., endothelial cells and smooth muscle cells) and proteins compose the vessel wall. The barrier component formed from the non-polymeric bio-absorbable cross-linked gel can prevent the interaction between the adjacent vessel surfaces, thereby preventing the initiation of the in-growth of the adjacent vessel surfaces while also preventing the initiation of the healing process by cells and proteins of the vessel walls. In this respect, the barrier component acts as in a patch-like manner to block cells and proteins of the vessel wall from interacting with adjacent vessel walls (i.e., the barrier component facilitates tissue separation) and provides a modulated healing effect that aids in the avoidance of fibrin activation and deposition and platelet activation and deposition.

In another non-binding example, the modulated healing effect can be attributed to the modulation (e.g., alteration, delay, retardation, reduction, detaining) of signaling between the cells and proteins that compose the vessel wall and various components of the bloodstream that would otherwise initiate the vascular healing process. Stated differently, at the site of vascular injury, the non-polymeric bio-absorbable cross-linked gel can modulate the interaction of cells of the vessel wall, such as endothelial cells and/or smooth muscle cells, with other cells and/or proteins of the blood that would otherwise interact with the damaged cells to initiate the healing process. Additionally, at the site of vascular injury, the non-polymeric bio-absorbable cross-linked gel can modulate the interaction of proteins of the vessel wall with other cells and/or proteins of the blood, thereby modulating the healing process.

The bio-absorbable cross-linked gel can be designed to maintain its integrity for a desired period of time, and then begin to dissolve and be absorbed into the tissue that it is surrounded by. Alternatively, the bio-absorbable cross-linked gel can be designed such that, to some degree, it is absorbed into surrounding tissue immediately after the barrier device is inserted in the subject. Depending on the formulation of the non-polymeric bio-absorbable cross-linked gel that makes up the barrier component, the barrier component is completely absorbed into surrounding tissue within a time period of 1 day to 24 months, e.g., 1 week to 12 months, e.g., 1 month to 10 months, e.g., 3 months to 6 months. Animal studies have shown resorption of the barrier component occurring upon implantation and continuing over a 3 to 6 month period, and beyond.

The oil component of the non-polymeric bio-absorbable cross-linked gel can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an adhesion-limiting agent. In addition, the fish oil maintains anti-inflammatory, non-inflammatory, or "modulated healing" properties as well. The present invention is not limited to with the use of fish oil as the naturally occurring oil for the non-polymeric bio-absorbable cross-linked gel. However, the description herein makes reference to the use of fish oil as one example embodiment. Other naturally occurring oils can be utilized in accordance with the present invention as described herein.

To understand further how the non-polymeric bio-absorbable cross-linked gel functions, a brief discussion is provided below concerning tissue injury and healing generally.

Vascular injury causing intimal thickening can be broadly categorized as being either biologically or mechanically induced. Biologically mediated vascular injury includes, but is not limited to, injury attributed to infectious disorders including endotoxins and herpes viruses, such as cytomegalovirus; metabolic disorders, such as atherosclerosis; and vascular injury resulting from hypothermia, and irradiation. Mechanically mediated vascular injury includes, but is not limited to, vascular injury caused by catheterization procedures or vascular scraping procedures, such as percutaneous transluminal coronary angioplasty; vascular surgery; transplantation surgery; laser treatment; and other invasive procedures which disrupt the integrity of the vascular intima or endothelium. Generally, neointima formation is a healing response to a vascular injury.

Wound healing upon vascular injury, and generally in non-vascular locations, occurs in several stages. The first stage is the inflammatory phase. The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, which are potent vasoconstrictors. This initial response helps to limit hemorrhage. After a short period, capillary vasodilatation occurs secondarily to local histamine release, and the cells of inflammation are able to migrate to the wound bed. The timeline for cell migration in a normal wound healing process is predictable. Platelets, the first response cells, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

As the inflammatory phase continues, more immune response cells migrate to the wound. The second response cell to migrate to the wound, the neutrophil, is responsible for debris scavenging, complement-mediated opsonization of bacteria, and bacteria destruction via oxidative burst mechanisms (i.e., superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, i.e., the proliferative phase.

The second stage of wound healing is the proliferative phase. Epithelialization, angiogenesis, granulation tissue formation, and collagen deposition are the principal steps in this anabolic portion of wound healing. Epithelialization occurs early in wound repair. At the edges of wounds, epidermis immediately begins thickening. Marginal basal cells begin to migrate across the wound along fibrin strands stopping when they contact each other (contact inhibition). Within the first 48 hours after injury, the entire wound is epithelialized. Layering of epithelialization is re-established. The depths of the wound at this point contain inflammatory cells and fibrin strands. Aging effects are important in wound healing as many, if not most, problem wounds occur in an older population. For example, cells from older patients are less likely to proliferate and have shorter life spans and cells from older patients are less responsive to cytokines.

Heart disease can be caused by a partial vascular occlusion of the blood vessels that supply the heart, which is preceded by intimal smooth muscle cell hyperplasia. The underlying cause of the intimal smooth muscle cell hyperplasia is vascular smooth muscle injury and disruption of the integrity of the endothelial lining. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and cytokines that result in the smooth muscle cell proliferation and migration. T-cells and macrophages also migrate into the neointima. This cascade of events is not limited to arterial injury, but also occurs following injury to veins and arterioles. Accordingly, the non-polymeric bio-absorbable cross-linked gels are able to modulate (e.g., alter, delay or prevent) one or more of the steps associated with intimal thickening following arterial injury, thereby preventing the heart disease and further vascular injury associated with vascular medical procedures.

Chronic inflammation, or granulomatous inflammation, can cause further complications during the healing of vascular injury. Granulomas are aggregates of particular types of chronic inflammatory cells which form nodules in the millimeter size range. Granulomas may be confluent, forming larger areas. Essential components of a granuloma are collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. The full extent of their functions is still unclear. Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged round the periphery of the cell, termed a Langhans-type giant cell; in other circumstances the nuclei are randomly scattered throughout the cytoplasm (i.e., the foreign body type of giant cell which is formed in response to the presence of other indigestible foreign material in the tissue). Areas of granulomatous inflammation commonly undergo necrosis.

Formation of granulomatous inflammation seems to require the presence of indigestible foreign material (derived from bacteria or other sources) and/or a cell-mediated immune reaction against the injurious agent (type IV hypersensitivity reaction).

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha and gamma-tocopherols can be used alone or in combination to provide an effective transport of a given compound to a given cell target, region, or specific tissue location.

As described previously, the process of modulated healing and cellular remodeling with non-polymeric bio-absorbable cross-linked gels involves different cascades or sequences of naturally occurring tissue repair in response to localized tissue injury, and it encompasses many different biologic processes, including epithelial growth, inhibition, proliferation and/or differentiation, connective fibrous tissue production and function, angiogenesis, and several stages of acute and/or chronic inflammation. Therefore, for example, by using the non-polymeric bio-absorbable cross-linked gel of the invention, which have modulated healing characteristics, one or more of the cascades or sequences of naturally occurring tissue repair are modulated (e.g., delayed), resulting in long-term stabilization of the areas treated by, for example, the non-polymeric bio-absorbable cross-linked gel-coated devices. The reversibly cross-linked gel has been shown experimentally in animal models not to produce or induce a protracted inflammatory response and to delay healing or formation of connective fibrous tissue following tissue injury. As such, the non-polymeric bio-absorbable cross-linked gel of the present invention can delay fibrin and platelet activation associated with the initial phase of vascular healing, and this delay will result in a lower long-term risk of vascular injury due to the formation of vulnerable plaques associated with the initial fibrin and platelet activation. Accordingly, the non-polymeric bio-absorbable cross-linked gel of the present invention provides an excellent absorbable cellular interface suitable for use with a surgical instrument or implantable medical device.

It should be noted that as utilized herein, the non-polymeric bio-absorbable cross-linked gel of the invention includes fish oil, as well as fish oil fatty acid. As used herein, fish oil fatty acid includes, but is not limited to, omega-3 fatty acid, fish oil fatty acid, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The biocompatible oils, including fish oil, are cured as described herein to form a hydrophobic cross-linked gel.

Likewise, it should be noted that to the extent utilized herein to describe the present invention, the term "vitamin E" and the term "alpha and gamma-tocopherols," are intended to refer to the same or a substantially similar substance, such that they are interchangeable and the use of one includes an implicit reference to both. Further included in association with the term vitamin E are such variations including but not limited to one or more of alpha and gamma-tocopherols, beta-tocopherol, delta-tocopherol, gamma-tocopherol, alpha-tocotrienol, beta-tocotrienol, delta-tocotrienol, gamma-tocotrienol, alpha and gamma-tocopherols acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha and gamma-tocopherols succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both mono-unsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-cross linked semi-solid. Hydrogenation can reduce or eliminate omega-3 fatty acids and any therapeutic effects (both anti-inflammatory and wound healing) they offer.

For long term controlled release applications, synthetic polymers, as previously mentioned, have been utilized in combination with a therapeutic agent. Such a combination provides a platform for the controlled long term release of the therapeutic agent from a medical device. However, synthetic polymer coatings have been determined to cause inflammation in body tissue. Therefore, the polymer coatings often must include at least one therapeutic agent that has an anti-inflammatory effect to counter the inflammation caused by the polymer delivery agent. In addition, patients that receive a synthetic polymer coating based implant must also follow a course of systemic anti-inflammatory therapy, to offset the inflammatory properties of the non-absorbable polymer. Typical anti-inflammatory agents are immunosuppressants and systemic delivery of anti-inflammatory agents can sometimes lead to additional medical complications, such as infection or sepsis, which can lead to long term hospitalization or death. Use of the non-polymeric bio-absorbable cross-linked gel described herein can negate the necessity of anti-inflammatory therapy, and the corresponding related risks described, because there is no inflammatory reaction to the non-polymeric bio-absorbable cross-linked gel.

FIGS. 1 through 9, wherein like parts are designated by like reference numerals throughout, illustrate example embodiments of non-polymeric biological and physical oil barrier components and barrier devices according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates an exemplary non-polymeric biological oil barrier device 100 in accordance with one embodiment of the present invention. The barrier device 100 is flexible, to the extent that it can be placed in a flat, curved, rolled, or contoured configuration. The barrier device 100 is implantable, for both short term and long term applications. Depending on the particular formulation of the barrier device 100, the barrier device 100 can be present after implantation for a period of hours to days, weeks, or possibly months. The barrier device 100 includes a barrier component 120 and one or more anchoring locations 130 that include openings 140 being disposed in, on or about the barrier component 120.

The barrier component 120 is formed of a cured oil component. The cured oil component can be either an oil, or an oil composition. The cured oil component can formed from a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an adhesion-limiting agent. In addition, the fish oil maintains anti-inflammatory or non-inflammatory properties as well. The present invention is not limited to formation of the film with fish oil as the naturally occurring oil. However, the following description makes reference to the use of a fatty acid based oil, such as, for example, fish oil. Other naturally occurring oils can be utilized in accordance with the present invention as described herein.

It should further be noted that FIG. 1 represents merely one embodiment of the barrier device 100. The barrier device 100 serves as a physical barrier as well as a biological oil barrier. The barrier device 100 can provide a non-inflammatory or anti-inflammatory barrier coating.

Using a number of different methods as described below, the barrier component 120 can consist of a biological oil that can be cured to create a non-polymeric cross-linked gel. Various degrees of curing can be used to vary the properties of the barrier device. In some embodiments, some of the biological oil is not cured, but is inter-dispersed within the cured oil. In other embodiments, the biological oil is substantial cured creating both a physical barrier or tissue separating barrier and a biological oil barrier. The physical barrier provides modulated healing and adhesion-limiting properties of the barrier component 120 as discussed herein.

Additional embodiments can include the provision of the substantially cured oil forming a physical barrier via a surface of the barrier component 120 and then a subsequent application of a substantially uncured biological oil as a top coat to create a more substantial biological oil barrier.

One aspect of the barrier component 120 mentioned above is that it has modulated healing and adhesion-limiting characteristics or properties. By adhesion-limiting, what is meant is a characteristic whereby the incidence, extent, and severity of postoperative adhesions induced by trauma, desiccational air injury, blunt dissection, or other lacerations or tissue injuries, between different tissue structures and organs and medical devices, is reduced (or changed). The adhesion-limiting characteristic barrier component 120 results from the bio-absorbable and non-polymeric materials used to form the barrier component 120.

More specifically, the barrier component 120 can provide a lubricious and/or physical non-adhesive surface against adhesion prone tissue. The barrier component 120 itself, in its partially or substantially cured configuration, can provide a physical adhesion-limiting barrier between two sections of tissue. When the naturally occurring oil, such as fish oil, is processed into a cross-linked gel or film creating the barrier component 120, the barrier component 120, with or without an addition coating of the oil in its natural state, provides an unexpected gliding surface against normally tacky moist tissue, which helps to reduce localized tissue abrasion injury and foreign body reaction. With less mechanical injury, there is less of an injury-induced inflammatory response, and less proliferative cell remodeling. The biological oil barrier created by the fatty acid oil derived barrier component 120 likewise provides anti-inflammatory and less tissue stimulating or biologically reactive properties, thus further reducing the occurrence of inflammatory response and adhesion related events due to inflammation. The surface of the barrier component 120 provides the modulated healing and mechanical adhesion-limiting characteristics. One of ordinary skill in the art will appreciate that different oil chemistry makeup, ingredients, and blends will have different healthier stimulus, adhesive limited effects, or cellular response reaction properties. The fatty acids used to form the oils into the gel or film can be modified to be more liquefied, emulsified, softer, more rigid, or more gel-like, solid, or waxy, as desired. Accordingly, the degree of modulated healing response and/or adhesive limiting and tissue reactive properties offered by the barrier component 120 can vary by modifying either the physical properties and/or chemical properties of the fatty acid containing oil. The modification of the oils from a more liquid physical state to a more gel-like or solid, but still flexible, physical state is further implemented through the curing process. As the oils are cured, especially in the case of fatty acid-based oils such as fish oil, reversible cross-links form creating a gel. As the curing process is performed over increasing time durations and/or increasing temperature or intensity conditions, more cross-links form transitioning the gel from a relatively wet liquid gel to a relatively solid-like, but still flexible, dry to the touch gel structure.

The barrier component 120 can be formed of the bio-absorbable material, such as naturally occurring fish oil, in accordance with an exemplary embodiment. The bio-absorbable properties of the naturally occurring oil enable the barrier component 120 to be absorbed slowly by the ingestion of the fatty acid components by cells of the body tissue (i.e., bio-absorbable). In exemplary embodiments, the bio-absorbable barrier component 120 contains lipids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Other naturally occurring and synthetic oils, such as vitamin E compounds, can also integrate into cellular membranes resulting in decreased membrane fluidity and cellular uptake.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha and gamma-tocopherols can be used alone or in combination to provide an effective transport of a given compound to a given cell target, region, or specific tissue location. Both fatty acids and alpha and gamma-tocopherols can be incorporated into the barrier layer of the present invention described herein. Accordingly, fatty acids and alpha and gamma-tocopherols can be combined in differing amounts and ratios to contribute to a barrier layer in a manner that provides control over the cellular uptake characteristics of the barrier layer and any therapeutic agents mixed therein.

For example, the type, blend, or amount of alpha and gamma-tocopherols can be varied in the barrier layer. Alpha and gamma-tocopherols are known to slow autoxidation in fish oil by reducing hydro peroxide formation, which results in a decrease in the amount of cross-linking in cured fish oil. In addition alpha and gamma-tocopherols can be used to increase solubility of drugs in the fish oil forming the barrier layer. Thus, varying the amount of alpha and gamma-tocopherols present in the barrier layer can impact the resulting formation. Alpha and gamma-tocopherols have been determined experimentally to provide a synergistic protective effect to therapeutic drugs and compounds during curing, which increases the resulting drug load in the barrier layer after curing. Furthermore, with certain therapeutic drugs, the increase of alpha and gamma-tocopherols in combination with fatty acids in the barrier layer serves to slow and extend the rate of drug release due to the increased solubility of the drug in the alpha and gamma-tocopherols component of the barrier layer. This reflects the cellular uptake inhibitor functionality of alpha and gamma-tocopherol compounds, in that the localized delivery and cellular uptake of the drug can be further modulated or controlled, slowed, and extended over time during barrier layer surface absorption by the localized tissue.

It should further be emphasized that the bio-absorbable nature of the barrier component 120 results in the barrier component 120 being completely absorbed through cell mediated fatty acid metabolic pathway over time by the localized cells in contact with the barrier component 120. There are no known substances in the barrier component 120 surfaces, or break down byproducts of the barrier component 120, that induce an inflammatory response during the naturally occurring fatty acid absorption process. The barrier component 120 is generally composed of, or derived from, omega-3 fatty acids bound to triglycerides, potentially also including a mixture of free fatty acids and, depending upon the drug, options combinations with vitamin E (alpha and gamma-tocopherols). The triglycerides are broken down by lipases (enzymes) which result in free fatty acids that can than be transported across cell membranes. Subsequently, fatty acid metabolism by the cell occurs to metabolize any substances originating with the barrier component 120. The bio-absorbable nature of the barrier component 120 results in the barrier component 120 modulating healing and limiting adhesion formation while being completely absorbed over time.

Although the present invention is bio-absorbable to the extent that the barrier component 120 experiences uptake and consumption into or through localized body tissues, in the specific embodiment described herein formed using naturally occurring oils, or synthetic equivalents, the exemplar oils are also lipid based oils. The lipid content of the oils provides a highly bio-absorbable barrier component 120. More specifically, there is a phospholipids layer in each cell of the body tissue. The fish oil, and equivalent oils, contain lipids as well. There is a lipophilic action that results where the lipids are attracted by each other in an effort to escape the aqueous environment surrounding the lipids.

A further aspect of the barrier component 120 is that the specific type of oil can be varied, and can contain elements beneficial to modulating healing. The barrier component 120 also breaks down during the absorption process into smaller fatty acid components, which can contributed to the localized tissue healing process involving cellular in-growth and remodeling of the barrier layer device. The addition of therapeutic agents to the barrier component 120 specifically for a localized drug delivery indication can be further utilized for additional beneficial biological effects, such as pain stimulation reduction or reduction in bacterial colonization, bio film formulation and adhesion, or localized infection minimization.

As described previously, the process of modulated healing and cellular remodeling, with barrier component 120 involves different cascades or sequences of naturally occurring tissue repair in response to localized tissue injury, and it encompasses many different biologic processes, including epithelial growth, inhibition, proliferation and/or differentiation, connective fibrous tissue production and function, angiogenesis, and several stages of acute and/or chronic inflammation. The reversibly cross-linked gel that forms the barrier component 120 has been shown experimentally in animal models not to produce or induce a protracted inflammatory response and to delay healing or formation of connective fibrous tissue following tissue injury. Likewise, the reversibly cross-linked gel that forms the barrier component 120 has exhibited a complimentary or synergistic modulated healing effect, which results in a less dense, but uniformly confluent cellular overgrowth of a porous implanted mesh structure with little to no fibrous capsule formation, which is otherwise commonly seen with conventional permanent mechanical barrier devices. Accordingly, the cross-linked gel that forms the barrier component 120 provides an excellent absorbable cellular interface suitable for use as a surgical implant.

Another aspect of the barrier component 120 mentioned above is that the barrier component 120 can contain therapeutic agents for local delivery to the body tissue in contact with the device. Therapeutic agents have been delivered to a localized target location within a human utilizing a number of different methods in the past. For example, agents may be delivered nasally, transdermally, intravenously, orally, or via other conventional systemic delivery methods. Local therapeutic delivery from a biological oil barrier layer device can be made to vary the therapeutic agent release rate (i.e., quick release or slow release) as part of the desired modulated healing effect of the barrier film surfaces.

As utilized herein, the phrase "therapeutic agent(s)" refers to a number of different drugs or biologically active agents available, as well as future agents that may be beneficial for use with the barrier layer of the present invention. Therapeutic agents can be added to the barrier layer 10, and/or the medical device in combination with the barrier layer 10 as discussed herein. The therapeutic agent component can take a number of different forms including additional modulated healing agents, adhesion-limiting agents, anti-oxidants, anti-inflammatory agents, anti-coagulant agents, thrombolysing agents, drugs to alter lipid metabolism, anti-proliferating agents, anti-neoplastics, tissue growth stimulants, functional protein/factor delivery agents, bactericidal agents, anti-biofilm adhesion agents, anti-infective agents, imaging agents, anesthetic agents, therapeutic agents, tissue absorption enhancers, antibiotics, germicides, anti-fungal agents, antiseptics, analgesics, prodrugs, and any additional desired therapeutic agents such as those listed in Table 1 below.

TABLE #1

| CLASS | EXAMPLES |
|---|---|
| Antioxidants | Alpha and gamma-tocopherols, fatty acids, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), fatty acids, leflunomide, NSAIDS, ibuprofen, acetaminophen, hydrocortizone acetate, hydrocortizone sodium phosphate, macrophage-targeted bisphosphonates, pimecrolimus, ISA247 |
| Growth Factor Antagonists | Angiopeptin, trapidil, suramin |
| Antiplatelet Agents | Aspirin, fatty acids, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate, abcximab, viperinex, tenectaplase |
| Drugs to Alter Lipid Metabolism (e.g. statins) | Fluvastatin, fatty acids, alpha and gamma-tocopherols, fish oil, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, fatty acids, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine, SAR943, TAFA93 |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes, polymer surgical adhesives |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibitation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium., sirolimus, rapamycin, minocycline, rifampin, cephalosporin, cefipime, metronidazole |
| Gene Delivery | Genes for nitric oxide synthase, human growth hormone, antisense oligonucleotides |
| Local Tissue perfusion | Alcohol, H2O, saline, fish oils, vegetable oils, liposomes, fatty acid derived from fish oils, vitamin E |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium, MRI contrast agents, PET/CT contrast agents, ultrasound contrast agents, biomarker agents |
| Anesthetic Agents | Lidocaine, benzocaine, bupivacaine, levobupivacaine, ropivacaine, xylocaine |
| Descaling Agents | Nitric acid, acetic acid, hypochlorite |
| Anti-Fibrotic Agents | Interferon gamma-1b, Interluekin-10 |

TABLE #1-continued

| CLASS | EXAMPLES |
| --- | --- |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase, cyclosporine |
| Tissue Absorption Enhancers | Fish oil, squid oil, omega 3 fatty acids, vegetable oils, lipophilic and hydrophilic solutions suitable for enhancing medication tissue absorption, distribution and permeation |
| Adhesion-limiting Agents | Hyaluronic acid, fatty acids, fish oil, vitamin E, human plasma derived surgical sealants, biodegradable hydrogels, surgical adhesives, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, silver acetate, sliver nitrate, furan derivatives, nitrofurazone, benzalkonium chloride, benzoic acid, salicylic acid, hypochlorites, peroxides, thiosulfates, salicylanilide |
| Antiseptics | Selenium, hydrogen peroxide |
| Analgesics | Bupivacaine, naproxen, ibuprofen, acetylsalicylic acid, levobupivacaine, ropivacaine, xylocaine |

Some specific examples of therapeutic agents useful in modulating or controlling localized tissue trauma response to cellular re-modeling with medical implants with barrier layers and/or modulated healing, and/or cellular proliferation involved in healing response include, modulated healing or anti-proliferating compounds including cerivastatin, cilostazol, fluvastatin, lovastatin, paclitaxel, pravastatin, m-Tor effecting compounds such as sirolimus, including, rapamycin, a rapamycin carbohydrate derivative (for example, as described in US Patent Application Publication 2004/0235762), a rapamycin derivative (for example, as described in U.S. Pat. No. 6,200,985), pro-drugs derived from rapamycin, analogs of rapamycin, including, everolimus, seco-rapamycin, seco-everolimus, and simvastatin. With systemic administration of such compounds orally, intravenously, or otherwise, the compounds are generally diluted throughout the body without specific localized delivery effect. There are drawbacks to a systemic delivery of a therapeutic agent, one of which is uncontrolled distribution that can occur when the therapeutic agent travels to all portions of the patient's body and creates undesired or unexpected effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher systemic dosing of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus (such as the barrier device of the present invention), directly by hand, or sprayed on the tissue, at a selected targeted tissue location of the patient that requires treatment. The therapeutic agent emits, or is otherwise delivered, from the medical device apparatus, and/or carrier (such as the barrier layer), and is applied to the targeted tissue location. The local delivery of a therapeutic agent enables a more concentrated and higher quantity of therapeutic agent to be delivered directly at the location of the implanted device, without having broader systemic distribution and potential remote target side effects.

Targeted local therapeutic agent delivery using a medical device with one or more barrier layers can be further broken into two categories, namely, short term and long term bioavailability to localized tissue ranging generally within a matter of seconds or minutes to a few days or weeks to a number of months. Conventionally, to achieve the long term bioavailability and delivery of a therapeutic agent to localized tissue, the therapeutic agent must be combined with a delivery agent, or otherwise formed with a physical impediment as a part of the medical device, to maximize absorption transfer of the therapeutic agent over an extended period of time while being absorbed by the local tissue.

Prior attempts to create surgically applied films and drug delivery platforms, such as in the field of soft tissue reinforcement, repair, or adhesion prevention, involving any soft tissue surgical intervention, make use of high molecular weight synthetic polymer base materials, including biodegradable and bio-erodable polymer films, non-absorbable polymer films, polymer gels and/or polymer coatings, to deliver therapeutic agents. Essentially, the polymer complexes in the platform release the drug or agent by allowing the drug to escape out from the polymer as it begins to dissolve at a predetermined rate once implanted at a location within the patient. Regardless of how beneficial to the local targeted tissue, most known polymer delivery materials release the therapeutic agent based release properties of the bulk polymer to elute the therapeutic agent or compound into adjacent or localized tissue and interstitial body fluids. Accordingly, the effect of the therapeutic agent is substantially local at the surface of the tissue making contact with the medical device having the coating. In some instances the effect of the therapeutic agent is further localized to the specific locations of, for example, stent struts or mesh that are anchored against the tissue location being treated. These prior approaches can create two different but undesirable local effects. One effect is the potential for an undesirable large quantity of drug into interstitial body fluids effecting bio-availability or cellular uptake of the drug, causing a localized or toxic effect. A second effect is an extended foreign body reaction to the carrier polymer after the therapeutic compound has been exhausted out of the polymer changing its local biochemical condition to adjacent tissue.

The barrier component 120 of the barrier device 100 can use biocompatible oils to form a non-polymeric bio-absorbable oil based therapeutic agent delivery platform, if desired. Furthermore, the barrier component 120 can be formed in a manner that creates the potential for controlled long term release of a therapeutic agent, while still maintaining the modulated healing, adhesion-limiting, and/or anti-inflammatory benefits of the oil component of the barrier component 120.

With the present invention, and in the field of soft tissue separation applications, and in part because of the lipophilic mechanism enabled by the bio-absorbable lipid based barrier component 120, the uptake of the therapeutic agent is facilitated by the delivery of the therapeutic agent to the cell membrane by the bio-absorbable barrier component 120, and not solely by drug release or elution out from the physical matrix used to form the barrier layer surfaces. Further, the therapeutic agent is not freely released into interstitial body fluids that are subject to systemic circulation, but rather, is delivered locally to the cells and tissue in contact with the barrier component 120. In prior configurations using polymer based coatings, the once immobilized drugs or agents are released out from the polymer structure at a rate regardless of the reaction or need for the drug on the part of the cells receiving the drug.

In addition, the bio-absorbable oil used to form the barrier component 120 is a naturally occurring oil, or synthetic equivalent, containing the omega-3 fatty acids (including DHA and EPA), and the process used for forming the barrier component 120 can be tailored to avoid causing detrimental effects to the beneficial properties of the omega-3 fatty acids, or at least effects too detrimental to have any lasting effect. Certain properties of the fatty acids may lose their effectiveness during curing, however other desired properties are maintained. Example embodiments illustrating the formation and different configurations of the barrier component 120 are provided herein.

Still referring to FIG. 1, the barrier device 100 includes anchoring locations 130. In this example, the anchoring locations 130 include openings 140 in the barrier component 120. The openings 140 can be created during the creation of the barrier component 120 and/or after the creation of the barrier component 120. The size and shape of the opening 140 can vary and may be based on the anatomical application. For example, the openings 140 take the form of, but are not limited to holes, slits, flaps, or the like.

The anchoring locations 130 assist in the attachment of the barrier device 100 to an anatomical area by providing a suitable area on the barrier device 100 for interfacing with an anchoring mechanism, such as a suture, a staple, a tack, adhesive (e.g., surgical glue), or the like. In one example, to anchor the barrier device 100 to an anatomical area, adhesive can be place at the anchoring locations 130, depicted as openings in FIG. 1, and adjacent tissues can be bound by the adhesive through the anchoring locations 130 such that the barrier device 100 is held in place. The properties of the barrier component 120 prevent the adhesive from adhering to the barrier component 120. Thus, the anchoring locations 130 that include openings 140 provide an area to facilitate the anchoring of the barrier device 100 to the anatomical area using an adhesive. By providing prefabricated anchoring locations 130, the barrier device 100 prevents a need to disrupt, stress, or weaken the barrier component 120 during attachment of the barrier device to the anatomical area.

To summarize, the barrier device 100 provides a physical and biological barrier for tissue separation composed of the barrier component 120 and anchoring locations 130 that provide an interface for anchoring mechanisms to assist in the attachment of the barrier device 100 to an anatomical area. The barrier component 120 of the present invention serves as a non-polymeric, therapeutically loadable physical barrier to modulate healing and/or limit adhesion formation between adjacent tissue as well as a biological oil barrier when the barrier component 120 is sufficiently cured and altered chemically. In accordance with the example embodiments described herein, the barrier component 120 is formed of a non-polymeric cross-linked gel, dry to the touch, which can be derived from fatty acid compounds. The fatty acids include omega-3 fatty acids when the oil utilized to form the barrier layer is fish oil or an analog or derivative thereof. As liquid pharmaceutical grade fish oil is heated, autoxidation occurs with the absorption of oxygen into the fish oil to create hydroperoxides in an amount dependent upon the amount of unsaturated (C═C) sites in the fish oil. However, the (C═C) bonds are not consumed in the initial reaction. Concurrent with the formation of hydroperoxides is the isomerization of (C═C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the barrier layer after the (C═C) bonds have substantially isomerized into the trans configuration. The (C═C) bonds can also form C—C cross-linking bridges in the glyceride hydrocarbon chains using a Diels-Alder Reaction. In addition to solidifying the barrier layer through cross-linking, both the hydroperoxide and (C═C) bonds can undergo secondary reactions converting them into lower molecular weight secondary oxidation byproducts including aldehydes, ketones, alcohols, fatty acids, esters, lactones, ethers, and hydrocarbons.

Accordingly, the barrier component 120 derived from fatty acid compounds, such as those derived from fish oil, include a reversible cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the gel. The barrier component 120 converts into fatty acid, short and long chain alcohol, and glyceride molecules, which are all non-inflammatory and likewise consumable by cells in the soft tissue to which the barrier device 100 is applied. Thus, the barrier component 120 is bio-absorbable.

Figure 2A:
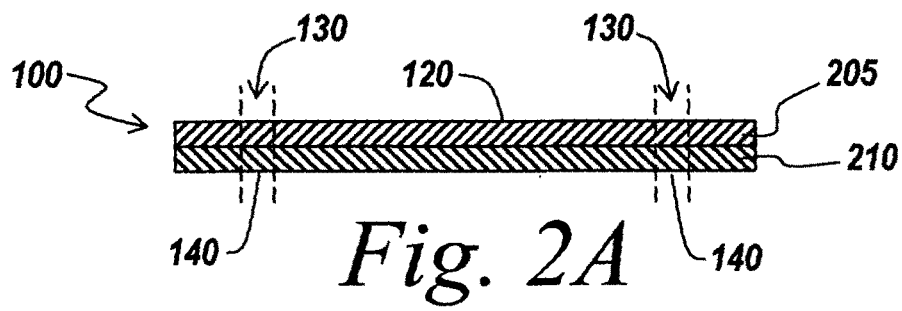
FIGS. 2A-C are cross-sectional views of the barrier device in accordance with one aspect of the present invention.
Figure 2B:
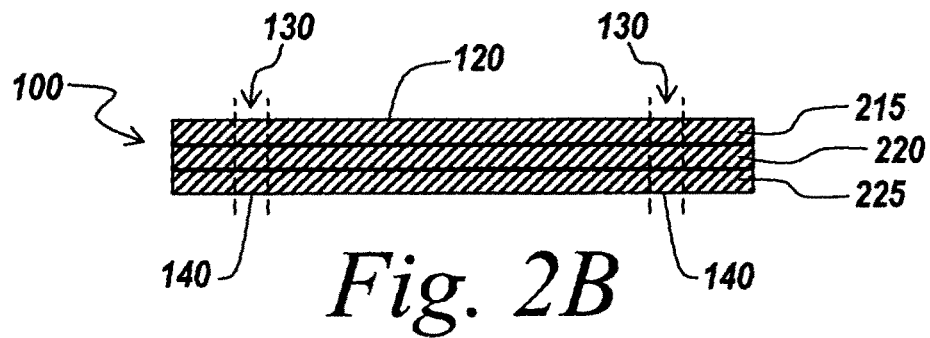
Figure 2C:
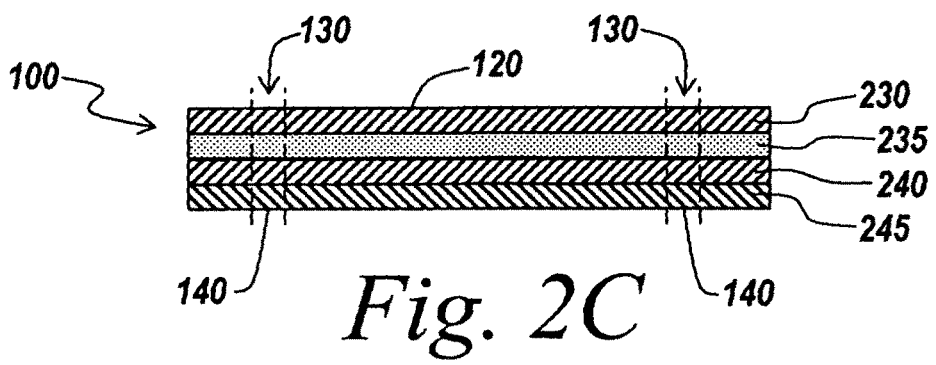

FIGS. 2A, 2B, and 2C illustrate side views of multiple different embodiments of the barrier device 100 when the barrier component 120 is cured into a flexible cross-linked gel. In FIG. 2A, a barrier component 120 is shown having two tiers, a first tier 205 and a second tier 210. The first tier 205 and the second tier 210 as shown are formed of different materials, although they can be formed of the same material. The different materials can be, for example, different forms of fish oil, different naturally occurring oils or biocompatible oils other than fish oil, or therapeutic components as will be discussed later herein. The different materials bind together to form the barrier component 120. The anchoring locations 130 include openings 140 that extend through the tiers 205 and 210 of the barrier component 120 to provide suitable areas of the barrier device 100 for assisting in the attachment of the barrier device 100 to an anatomical area using a suitable anchoring mechanism.

FIG. 2B shows another exemplary barrier device 100 that is consists of the barrier component 120 having a first tier 240, a second tier 260, and a third tier 280 and anchoring locations 130 that include openings 140 extending through the tiers 215, 220 and 2225 of the barrier component 120 to provide a suitable area of the barrier device 100 for assisting in the attachment of the barrier device 100 to an anatomical area. In this example, each of the tiers 215, 220, and 225 are formed of the same material, although they can be formed of different materials. The plurality of tiers indicates the ability to create a thicker barrier component 120 if desired. The greater the number of tiers, the thicker the resulting film. The thickness of the barrier component 120 can have an effect on the overall strength and durability of the barrier component 120. A thicker film can be made to be generally stronger and more durable, or can be made to be weaker and less durable, depending on the clinical application. In addition, the thickness of the barrier component 120 can also affect the duration of time that the barrier component 120 lasts and provides modulated healing or limited adhesion after implantation. A thicker barrier component 120 provides more material to be absorbed by the body, and thus will last longer than a thinner barrier component 120 of the same chemical makeup, which ultimately influences the implementation of the modulated healing. One of ordinary skill in the art will appreciate that the thickness of the barrier component 120 can vary both by varying the thickness of each tier 215, 220, and 225, and/or by varying a number of tiers. Accordingly, the present invention is not limited to the particular tier combinations illustrated.

FIG. 2C shows another exemplary embodiment of the barrier device 100 that consists of the barrier component 120, having four tiers, a first tier 230, a second tier 235, a third tier 240, and a fourth tier 245 and anchoring locations 130 that include openings 140 that extend through the tiers 230, 235, 240, and 245 of the barrier component 120 to provide a suitable area of the barrier device 100 to assist in the attachment of the barrier device 100 to an anatomical area. In this example, the first tier 230 and the third tier 240 are formed of the same material, while the second tier 235 and the fourth tier 245 are formed of a material different from each other and different from that of the first tier 230 and the third tier 240. Accordingly, this embodiment illustrates the ability to change the number of tiers, as well as the material used to form each of the tiers 230, 235, 240, and 245. Again, the different materials can be derived from different forms of fish oil, different naturally occurring oils other than fish oil, or therapeutic components as will be discussed later herein.

FIGS. 3A through 3F show additional embodiments or configurations of the barrier layer 100. FIG. 3A depicts an embodiment of the barrier device 100 that includes the barrier component 120 in a circular configuration with anchoring locations 130 that include openings 140 of varying shapes and sizes that extend through the barrier component 120. FIG. 3B depicts an embodiment of the barrier device 100 that includes a barrier component 120 in an oval configuration with anchoring locations 130 that include openings 140 of varying shapes and sizes extending through the barrier component 120. FIG. 3C depicts the barrier device 100 that includes the barrier component 120 in a U-bend configuration with anchoring locations 130 that include openings 140 of varying shapes and sizes that extend through the barrier component 120. FIG. 3D depicts an embodiment of the barrier device 100 that includes the barrier component 120 in a square configuration having a circular aperture 310 and includes anchoring locations 130 that include openings 140 of varying shapes and sizes that extend through the barrier component 120. FIG. 3E depicts another exemplary embodiment of the barrier device 100 that includes the barrier component 120 in a wave configuration with anchoring locations 130 that include openings 140 extending through the barrier component 122. FIG. 3F depicts still another embodiment of the barrier device 100 that includes the barrier component 120 in an irregular shape configuration with anchoring locations 130 that include openings 140 of varying shapes and sizes extending through the barrier component 120.

Each of the embodiments of the barrier device 100 represent different types of possible configurations of the barrier device 100. The configurations illustrated are by no means the only possible configurations for the inventive barrier device 100. One of ordinary skill in the art will appreciate that the specific shape or configuration of the barrier device 100 can vary as desired. A more prevalent configuration is the rectangular or oblong configuration of FIG. 1. However, FIGS. 3A through 3F illustrate a number of different alternative embodiments, and indicate some of the many possible configurations.

FIG. 4 is a flowchart illustrating one example method for the formation of the barrier device 100. A surface is provided having a release agent (step 400). The surface can be configured with depressed and/or elevated regions to facilitate the formation of the anchoring locations 130 that include openings 140. Alternatively, the surface may be configured such that the anchoring locations 130 are not formed by the surface. The surface can be prepared by the application of the release agent, or the release agent can be pre-existing. The release agent can be a number of different solutions, including for example, polyvinyl alcohol (PVA). The release agent can be applied in a number of different ways as well, including but not limited to casting, impregnating, spraying, dipping, coating, painting, and the like. It should be noted that the release agent can be applied optionally to the surface immediately prior to the remaining steps or well in advance of the remaining steps, so long as when the remaining steps are executed there is a release agent on the surface. It should further be noted that the need of an optional release agent can be eliminated if the surface itself has inherent characteristics similar to one having a release agent. Specifically, the surface can instead have a Teflon® coating, or other similar more permanent release surface. In such an instance, there is no need for a release agent, or subsequent removal of the release agent from the barrier layer formed.

An oil component is applied to the surface on top of the release agent (step 402). As noted previously, the oil component can be a naturally occurring oil, such as fish oil, cod liver oil, cranberry oil, or other oils having desired characteristics. In addition, the oil component can be an oil composition, meaning a composition containing oil in addition to other substances. For example, the oil composition can be formed of the oil component in addition to a solvent and/or a preservative. Solvents can include a number of different alternatives, including ethanol or N-Methyl-2-Pyrrolidone (NMP). The preservative can also include a number of different alternatives, including vitamin E. One of ordinary skill in the art will appreciate that there are a number of different solvents and preservatives available for use with the oil component to form the oil composition, and as such the present invention is not limited to only those listed in the examples herein. The solvent can be useful to alter the physical properties of the oil, as well as prepare the oil for combination with a therapeutic agent as described below. The preservative can also be useful in altering the physical properties of the oil component, as well as protecting some of the beneficial properties of the oil component during certain curing processes. Such beneficial properties include the healing and anti-inflammatory characteristics previously mentioned.

The oil component can be combined with one or more therapeutic agents to form an oil composition. Thus, if the added therapeutic benefit of a particular therapeutic agent or agents is desired, the therapeutic agent(s) can be added to the oil component prior to application to the surface, along with the oil component during application to the surface (including mixing with the oil component prior to application), or after the oil component has been applied (step 404). The different alternatives for adding the therapeutic agent(s) are determined in part based on the desired effect and in part on the particular therapeutic agent(s) being added. Some therapeutic agents may have reduced effect if present during a subsequent curing step. Some therapeutic agents may be more useful intermixed with the oil component to extend the release period, or applied to the surface of the oil component, resulting in a faster release because of increased exposure. One of ordinary skill in the art will appreciate that a number of different factors, such as those listed above in addition to others, can influence when in the process the therapeutic agent is added to the oil component, or the barrier component 120. Accordingly, the present invention is not limited to the specific combinations described, but is intended to anticipate all such possible variations for adding the therapeutic agent(s).

For example, if 80% of a therapeutic agent is rendered ineffective during curing, the remaining 20% of therapeutic agent, combined with and delivered by the barrier can be efficacious in treating a medical disorder, and in some cases have a relatively greater therapeutic effect than the same quantity of agent delivered with a polymeric or other type of coating or barrier. This result can be modified with the variance of alpha and gamma-tocopherols to protect the therapeutic agent during the curing process, and then slow and extend the delivery of the therapeutic agent during absorption of the barrier layer into the tissue.

The oil component (e.g., oil or composition if mixed with other substances) is then hardened into the barrier component 120 (step 406). The step of hardening can include hardening, or curing, such as by introduction of UV light, heat, oxygen or other reactive gases, chemical curing, or other curing or hardening method. The purpose of the hardening or curing is to transform the more liquid consistency of the oil component into a more solid film, while still maintaining sufficient flexibility to allow bending and wrapping of the film as desired.

After the barrier component 120 has formed, another determination is made as to whether therapeutic agents should be applied to the film. If desired, the therapeutic agent(s) is added to the barrier component 120 (step 408).

Subsequently, if the surface used for forming the barrier device 100 was configured to form the anchoring locations 130 that include openings 140, the barrier device 100 is removed from the surface (step 412). Alternative, if the surface was not configured to form the anchoring locations 130 that include openings 140 are subsequently formed (step 410). In this case, the openings 140 can be formed by cutting or drilling sections of the formed barrier component 120 or the openings 130 can be formed by any other suitable mechanism for forming anchoring locations 130 that include openings 140 in the barrier component 120. After the anchoring locations 130 that include openings 140 are formed (step 410), the barrier device 100 is removed from the surface (step 412).

Once again, there is opportunity to apply a therapeutic agent(s) to the barrier device 100 on one or both sides of the barrier device 100. If such therapeutic agent(s) is desired, the therapeutic agent(s) is applied (step 414). The additional therapeutic agent can also be applied in the form of a non-cured or minimally cured oil, such as fish oil. The oil can likewise include other therapeutic agents mixed therewith. The resulting structure of such an application forms the underlying barrier component 120 that is cured to form the film, with a top coating of oil and potentially additional therapeutic agent layered on top. This structure enables the provision of a short term release of therapeutic from the oil top layer combined with a longer term release from the cured barrier component 120, which takes more time to degrade.

After application of the therapeutic agent(s), or after the barrier device 100 is removed from the surface, the barrier device 10 is sterilized (step 416). The sterilization process can be implemented in a number of different ways. For example, sterilization can be implemented utilizing ethylene oxide, gamma radiation, E beam, steam, gas plasma, or vaporized hydrogen peroxide (VHP). One of ordinary skill in the art will appreciate that other sterilization processes can also be applied, and that those listed herein are merely examples of sterilization processes that result in a sterilization of the barrier device 100, preferably without having a detrimental effect on the barrier device 100.

It should be noted that the oil component can be added multiple times to create multiple tiers in forming the barrier component 120. For example, if a thicker barrier component 120 is desired, additional tiers of the oil component can be added after steps 400, 404, 406, 408, 412, or 414. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Figure 5A:
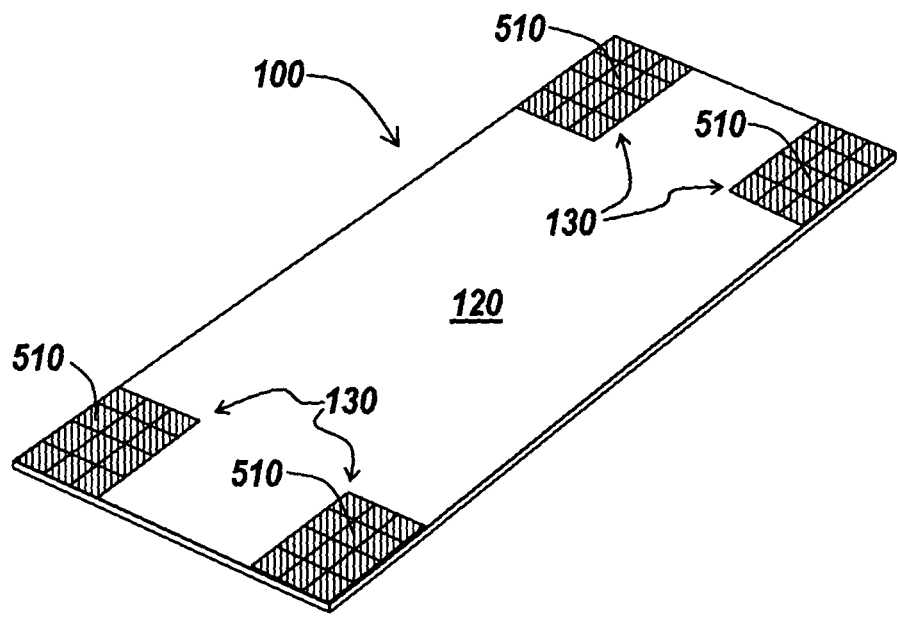
FIGS. 5A-F depict various exemplary barrier devices in accordance with exemplary embodiments of the present invention.
Figure 5B:
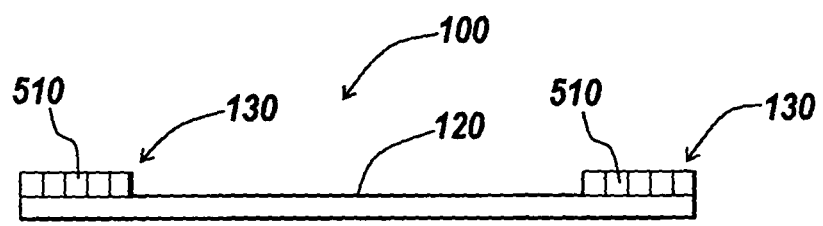

FIG. 5A depicts an exploded view of one embodiment of the barrier device 100 and FIG. 5B depicts the coupling between components of the barrier device 100. The barrier device 100 includes the barrier component 120 and one or more anchoring locations 130 that include anchor elements 510. The barrier component 120 can encapsulate the anchor elements 510. The anchor elements 510 can be composed of a biocompatible material, such as polypropylene, however other biocompatible materials can be utilized, such as a porous mesh or porous polymer film formed of the same or similar substance as the barrier component 120 (i.e., oil based). One form of a material that is suitable for use as the anchor element(s) 510 is a surgical mesh. Mesh is merely one example medical device that can be entirely impregnated or 100% coupled with the barrier component 120. In some instances, it can be useful to have one side of the fully impregnated anchor elements 510 to be made having an irregular or non-smooth surface to encourage faster or less delayed tissue in-growth, and the other side of the anchor elements 510 with a smoother barrier component 120 surface. The smoother side of the barrier component 120 can exhibit a more uniform tissue contacting support for gliding on tissue without dragging or pulling on the underlying tissue during installation, a smooth surface which limits the rate and/or attachment on adjacent tissue, a smooth surface which restricts the rate of in-growth, and provides improved adhesion-limiting, anti-inflammatory, and/or non-inflammatory surface properties. The coupling of the barrier component 120 with the anchor element(s) 510 achieves such a device. In the example illustrated in FIG. 5A, the anchor elements 510 are rectangular pieces of mesh that are position at the corners of the barrier layer device 100, although anchor elements 510 can vary in shape, size and location.

The anchor elements 510 provide a surgeon or other medical user with adequate area to interface with anchoring mechanisms such as, sutures, tacks, adhesive, and the like, to hold the barrier device 100 in place in the patient. Since the barrier component 120 generally has anti-adhesive properties, the anchor elements 510 at the anchoring locations 130 can be used to hold the barrier device 100 in place while the barrier component 120 breaks down and is absorbed by the patient. This prevents the barrier device 100 from shifting after implantation improving the effectiveness of the barrier component 120.

Figure 5C:
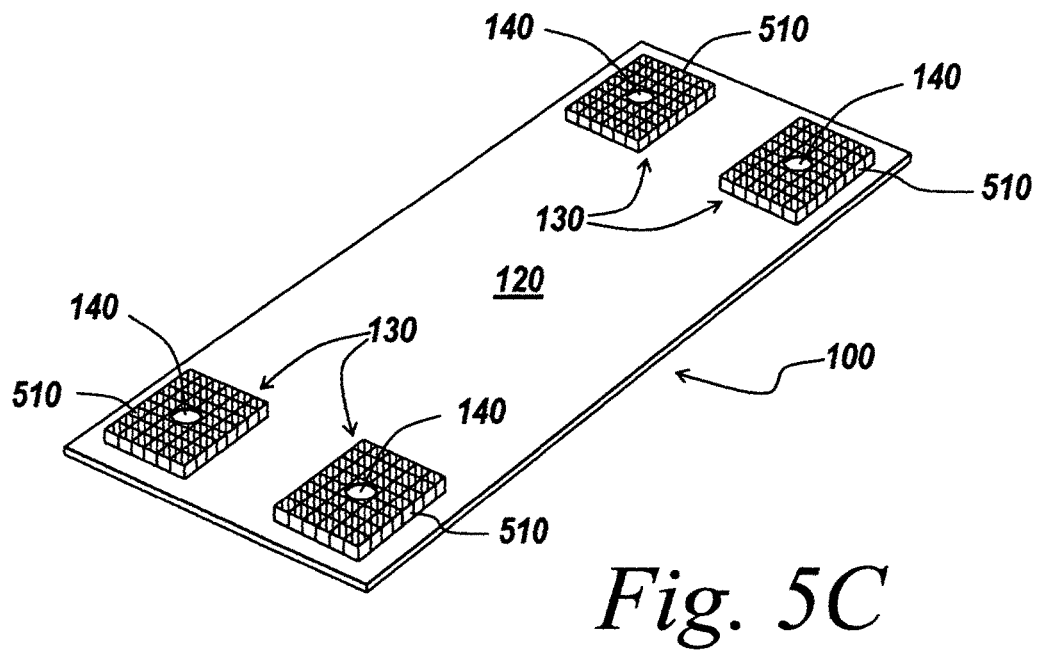

In some embodiments, the anchor elements 510 can have openings, such as holes, slots, slits, flaps, etc., in them, or one or more of the anchor elements 510 can be formed to substantially surround an opening, such as hole, slot, slit, flap, etc., in the barrier component 120. FIG. 5C depicts one embodiment of the barrier device that include the barrier component 120 and anchoring locations 130 that include anchor elements 510 and openings 140 that extend through the barrier component 120. In this example, the barrier device 100 can be placed between soft tissues and/or bone and can be held in place using an anchoring mechanism, such as an adhesive (e.g., surgical glue), suture, tack, staple, or the like. The anti-adhesive properties of the barrier component 120 prevent adhesives from adhering to it. In some embodiments where an adhesive is used, the adhesive can be used to couple a small amount of soft tissue on each side of the barrier device 100 to hold the barrier device 100 in place as the barrier device 100 breaks down.

The anchor elements 510 can provide increased durability to the anchoring locations 130. The anchor elements 510 can reduce or eliminate the occurrence of distortions, tears or other deformations around the anchoring locations.

Figure 5D:
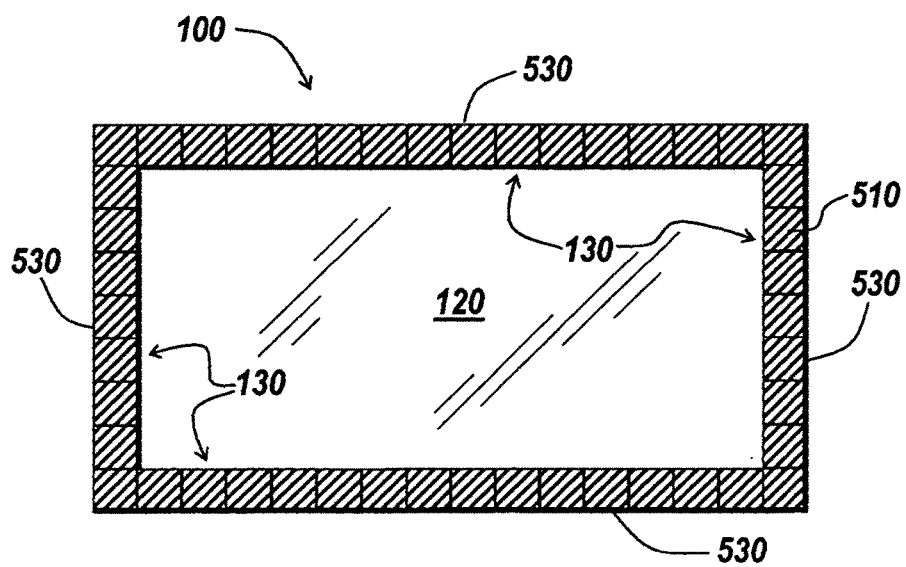

In another embodiment, the anchor element(s) 510 can form a frame around a perimeter of the barrier component 120, as depicted in FIG. 5D. In this example, the frame follows along a perimeter 530 of the barrier component 120. Thus, with a rectangular or oblong shaped barrier device 100, the frame of the anchor element(s) 510 likewise is rectangular or oblong in shape. One of ordinary skill in the art will appreciate that in some embodiments the shape of the anchor element(s) 510 depends upon the shape of the underlying barrier component 120 or desired anatomical application. Essentially, the function of the anchor element 510 is to provide an area on the barrier device 100 to provide for attaching the barrier device 100 to an anatomical area and to provide added structural integrity and strength at the area of the barrier device 100 where a surgeon is most likely to use an anchoring mechanism, such as adhesive, a suture, a staple, a tack, or the like.

Figure 5E:
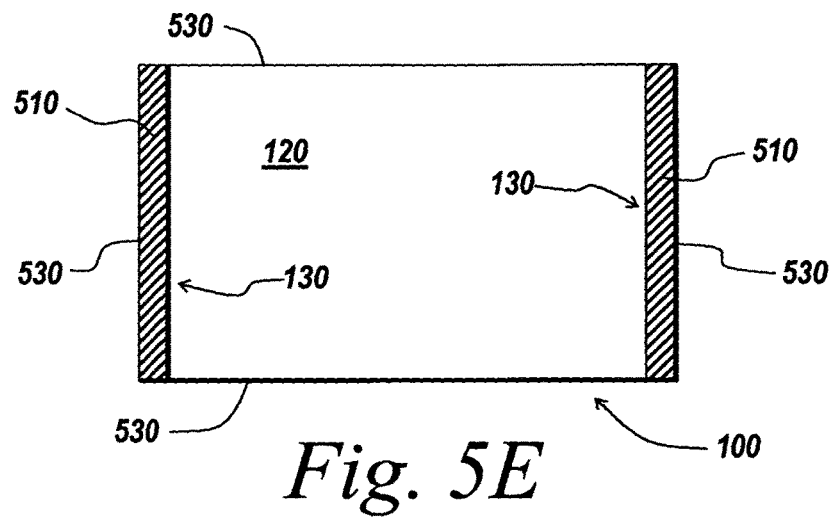
Figure 5F:
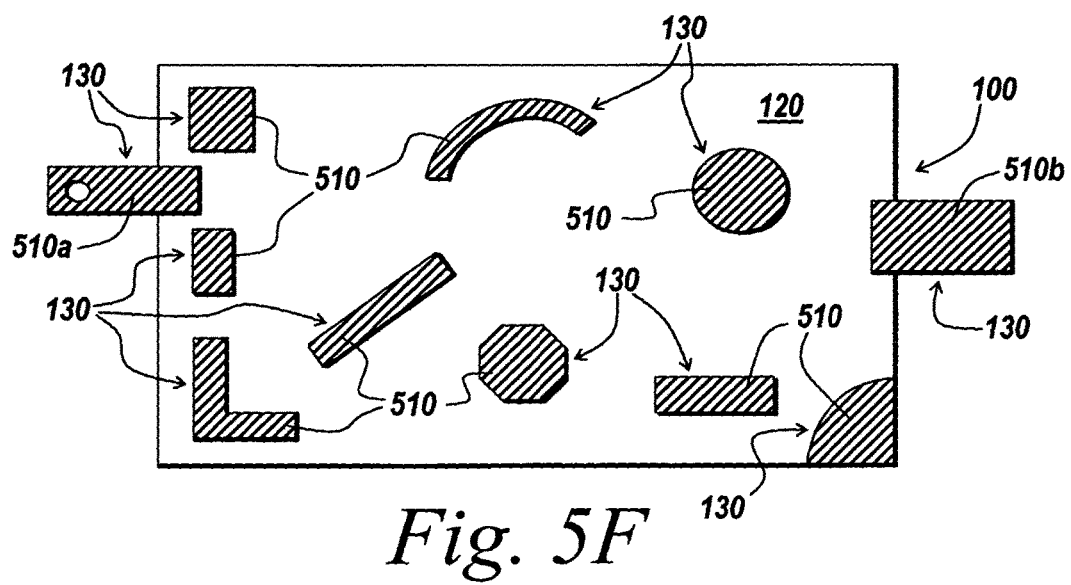

The anchor elements 510 can also extend along one or more edges on a perimeter 530 of the barrier device 100, as depicted in FIG. 5E. In some cases, discussed in more detail below the barrier device 100 is used to substantially encompass an anatomical area The above examples depicted in FIGS. 5A-E depict exemplary embodiments of the barrier device 100 and various arrangements of the anchor elements 510. Additional embodiments of the barrier device 100 and arrangements of anchor elements 510 can be implemented. For example, FIG. 5F depicts another arrangement of anchor elements 510 that can be implemented. For example, anchor elements 510 can take the form of tabs 510a and 510b that extend beyond the perimeter 530 of the barrier device 100. Further, the anchor elements 40e can vary in shape, size, structure, forms, symmetries, non-symmetries, configurations, locations on the barrier device 100, etc. and the number, size, and location of the anchor elements 510 can vary based on an anatomical application, a size of the barrier layer device 100, etc.

The duration of the anchoring function is preferably until modulated healing and cellular growth has transformed to a point whereby the anatomical area protected by the barrier device 100 has substantially healed and the risk of the separated soft tissues and/or bones growing together has subsided.

Figure 6A:
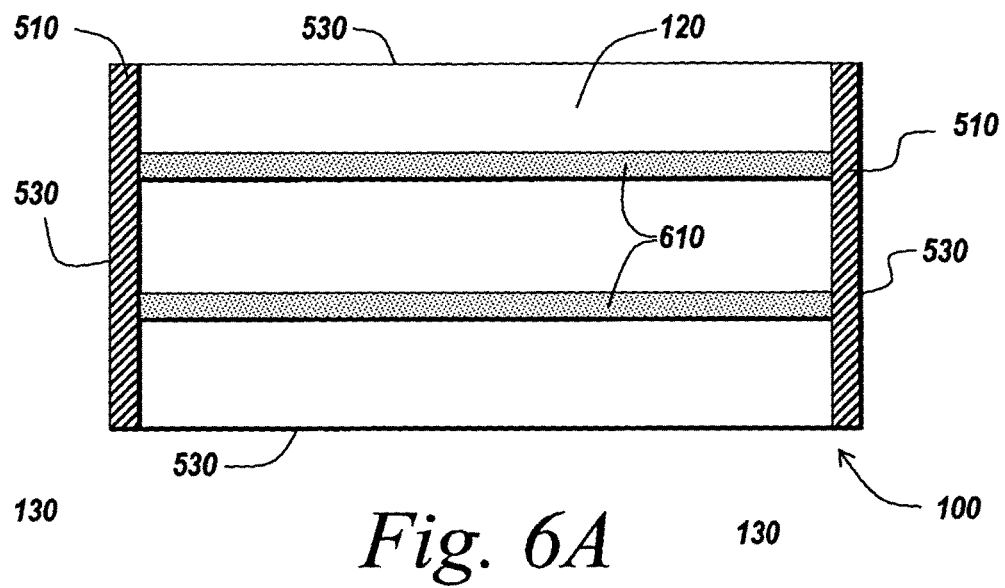
FIGS. 6A-B depict other exemplary embodiments of barrier devices that include reinforcing truss structures to provide additional support to a barrier device.
Figure 6B:
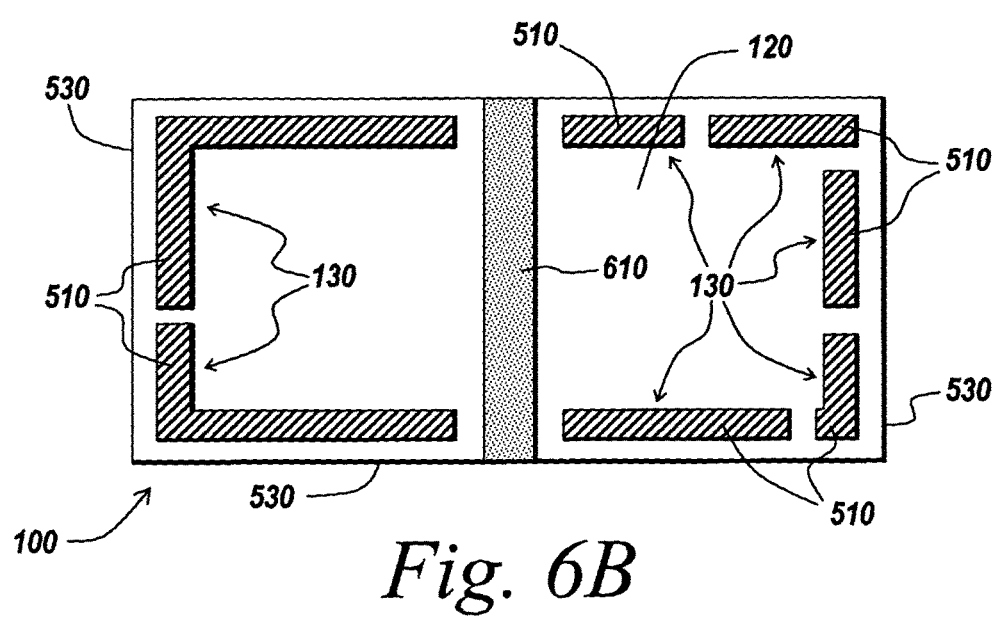

In some embodiments, a truss structure can be included in the barrier layer device. FIGS. 6A-B depict embodiments the barrier device 100 that include anchor elements 510. The barrier device 100 also includes one or more truss structures 610. The term "truss structure," as used herein, refers to a supportive structure that aids in reducing or eliminating the effects of tension, compression, shearing, bending, etc., on the barrier device. In FIG. 6A, the truss structures 610 extend across an interior surface of the barrier component 120 and towards a perimeter 530 of the barrier component 120, but do not contact the perimeter 530. In FIG. 6B, the truss structure 610 extends towards and contacts the perimeter 530 of the barrier component 120. The truss structures 610 provide added strength to the barrier device 100 to prevent the barrier device 100 from moving after it is implanted in a patient. The truss structures 610 can be formed using a biocompatible material, such as polypropylene, however other biocompatible materials can be utilized, such as a porous mesh or porous polymer film formed of the same or similar substance as the barrier component 2 (i.e., oil based). The truss structures 610 cover sections of the barrier component such that the area of the barrier component 120 that is covered by the truss structures 610 is less than the surface area of the barrier component 120. The location, configuration, number, size, etc., of the truss structures 610 can vary based on the size, shape, desired anatomical application, etc., of the barrier devices discussed herein. The truss structures 610 provide added support to the barrier component 120 so that as the barrier component 120 breaks down and is absorbed, the barrier component 120 does not shift. Additionally, the truss structures 610 also help eliminate or reduce effects of stresses, such as tension, compression, shearing, bending, etc., that can be applied to the barrier device 100.

In some instances, the truss structures 610 and anchor elements 510 can be formed as single biocompatible structure, such as a surgical mesh. In other instances, the truss structures 610 and the anchor elements 510 can be separate biocompatible structures. In addition, the truss structures 610 and anchor elements 510 can be composed of different material and/or can have varying rigidity. In some embodiments, the barrier device 100 does not include anchor elements 510 in combination with the truss structures 610, but rather the barrier device 100 includes anchoring locations 130 that include openings 140 in combination with the truss structures 610. In other embodiments, a combination of openings 140, anchor elements 510 and truss structures 610 can be implemented.

Figure 7:
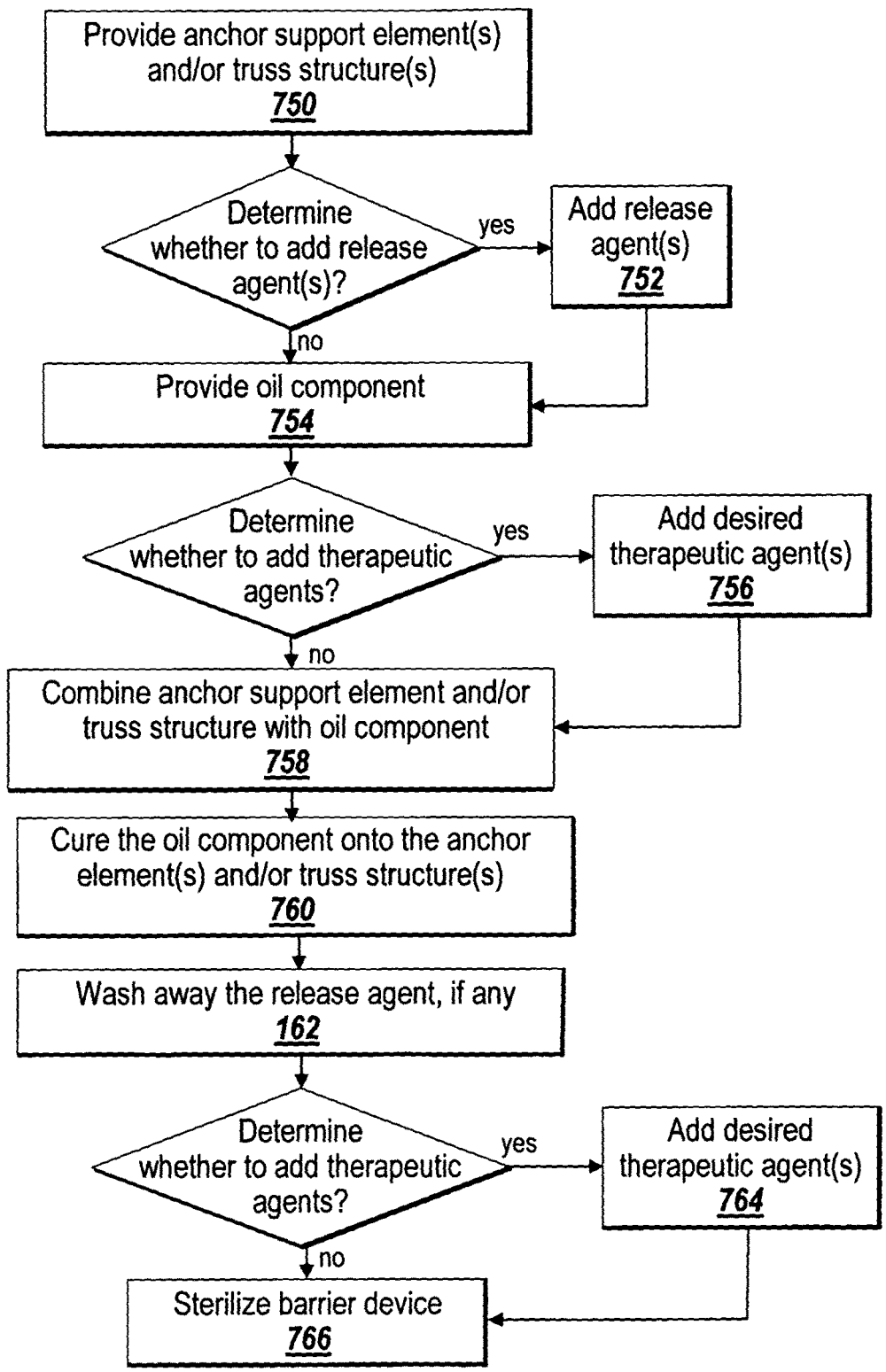
FIG. 7 is a flow chart illustrating a method of combining a barrier component with a medical device, in accordance with one embodiment of the present invention.

FIG. 7 is a flowchart illustrating one example method for forming an embodiment of the barrier device 100. Anchor element(s) 510 and/or truss structure(s) 610 are provided (step 750). The anchor element(s) 510 and/or truss structure(s) 610 can be a bio compatible material and can take the form of a mesh.

A determination is made as to whether a release agent should be added to the anchor element(s) 510 and/or truss structure(s) 610 to aid in removing the anchor element(s) 510 and/or the truss structure(s) 610 from their location (e.g., on a surface) after combination with the barrier component 120. If a release agent is required, the release agent is applied to the anchor element(s) 510 and/or truss structure(s) 610 (step 752). An example release agent for such an application is polyvinyl alcohol.

Additionally, an oil component is provided that can subsequently be cured to form the barrier component 120 (step 754). The oil component can be combined with one or more therapeutic agents to form an oil composition. If one or more therapeutic agents are desired, the therapeutic agents are added to the oil component (step 756). The therapeutic agent(s) can be added to the oil component by mixing the therapeutic agents with the oil component prior. The different alternatives for adding the therapeutic agent(s) are determined in part based on the desired effect and in part on the particular therapeutic agent(s) being added. Some therapeutic agents may have reduced effect if present during a subsequent curing step. Some therapeutic agents may be more useful intermixed with the oil component to extend the release period, or applied to the surface of the oil component, resulting in a faster release because of increased exposure.

Subsequent to the addition of therapeutic agents or if no therapeutic agents are added, the anchor element(s) 510 and/or truss structure(s) 610 can then be combined with the oil component (step 758). Depending on the particular material or materials used to form the anchor element(s) 510 and/or truss structure(s) 610, the combination with the oil component can be implemented more efficiently by either applying the oil component to the anchor element(s) 510 and/or truss structure(s) 610, or placing the anchor element(s) 510 and/or truss structure(s) 610 on the oil component. For example, in the case where the anchor element(s) 510 are in the form of a mesh, the anchor element(s) 510 can be placed on top of the oil component, or the oil component can be placed on top of the anchor element(s) 510. Additionally, as discussed herein, the barrier component 120 can be formed on or around the anchor element(s) 510 and/or truss structure(s) 610 and in some instances can encapsulate the anchor element(s) 510 and/or truss structure(s) 610.

The anchor element(s) 510, truss structure(s) 610 and the oil component are then cured to create a bond to form the barrier device 100 (step 760). The curing process can be one of several known processes, including but not limited to applying heat, or UV light, or chemical curing, to cure the barrier component 120. In the instance of the curing occurring with the liquid form of the barrier component 120 that is poured over and/or through the anchor element(s) 510 and/or truss structure(s) 610, the curing creates a coating in and around the anchor element(s) 510 and/or truss structure(s) 610, encapsulating the anchor element(s) 510 and/or truss structure(s) 610 within the barrier component 120. After curing, if there is any release agent present, the release agent is washed away using water, or some other washing agent (step 762).

After the release agents are washed away, addition therapeutic agents may be added to coat the barrier device 100. If it is determined that therapeutic agents are to be added, the therapeutic agents can be applied to the barrier device 100 (step 764). Subsequent to the addition of therapeutic agents or if no therapeutic agents are added, the barrier device 100 is sterilized (step 766).

Figure 8:
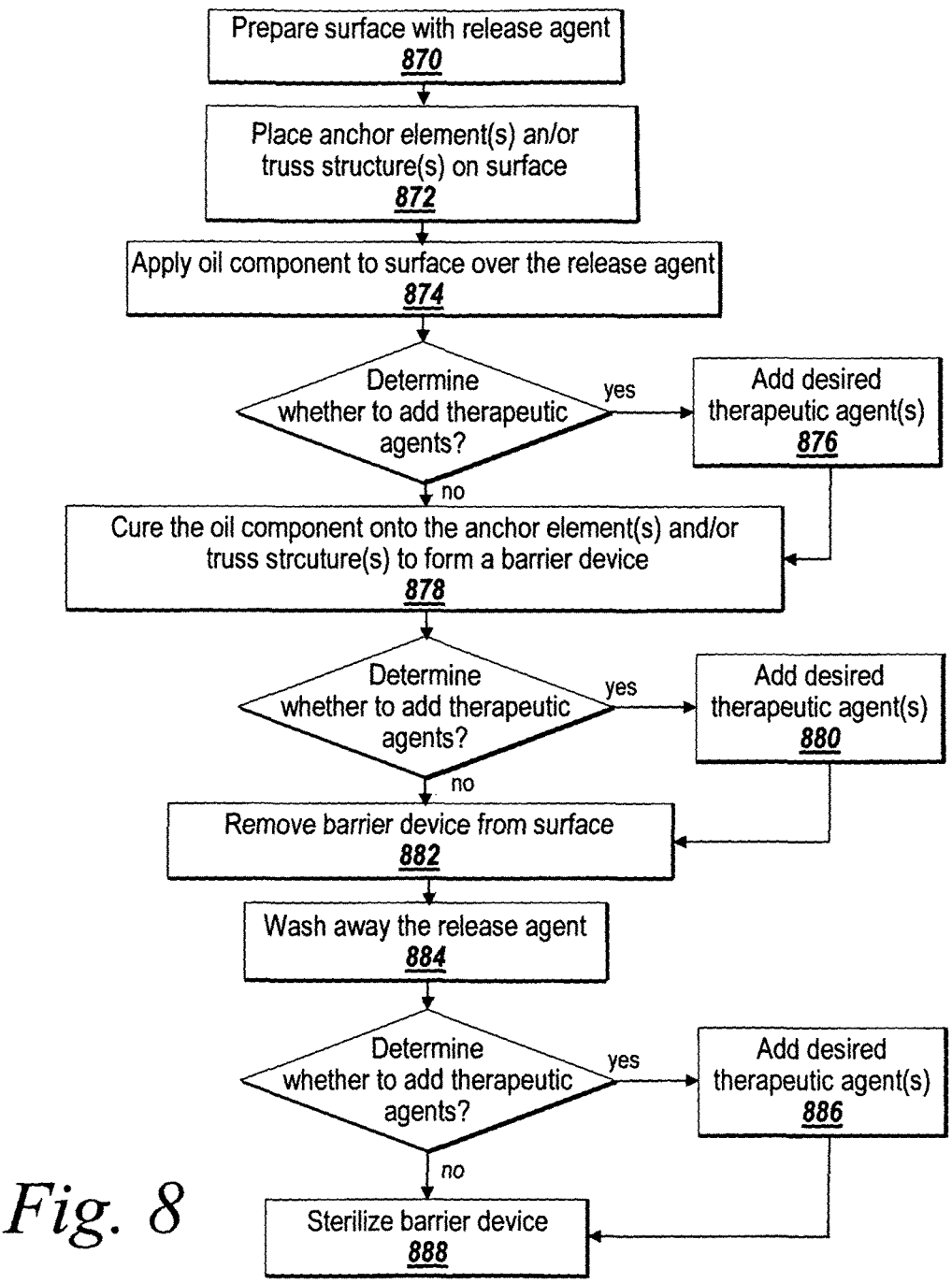
FIG. 8 is a flow chart illustrating another variation of the method of FIG. 7, in accordance with one embodiment of the present invention.

FIG. 8 is a flowchart illustrating another example method of forming the barrier layer device 100. A surface is prepared with a release agent, such as PVA (step 870), as needed. The anchor element(s) 510 and/or truss structure(s) 610 are placed on the surface (step 872). In the example embodiment, the anchor element 510 and/or truss structure(s) 610 are in the form of a mesh. The oil component is applied to the anchor element(s) 510 and/or truss structure(s) 610 (step 874). The oil component is poured or sprayed onto the anchor element(s) 510 and/or truss structure(s) 610. The oil component falls substantially to a bottom side of the anchor element(s) 510 and/or truss structure(s) 610 (due to gravitational pull), leaving a thinner coating or amount at a top side of the anchor element 510 and/or truss structure(s) 610, but still substantially encapsulating the anchor element(s) 510 and/or truss structure(s) 610 within the liquid of the oil component. Such a coating process provides that the barrier component 120 forms on all sides of the anchor element(s) 510 and/or truss structure(s) 610 when the oil component is cured.

The oil component can be mixed with therapeutic agents prior to applying the oil component to the anchor element(s) 510 and/or truss structure(s) 610. Alternatively, if one or more therapeutic agents are desired to be added to the oil component after the oil component is applied to the anchor element(s) 510 and/or truss structure(s) 610, therapeutic agents can be added (step 876).

In either case, the combined oil component, anchor element(s) 510 and/or truss structure(s) 610 are then cured (step 878) using methods such as application of heat, UV light, oxygen and other reactive gases, chemical cross-linker, or hardening processes, to form the barrier device 100 having the barrier component 120 in combination with the anchor element(s) 510 and/or truss structure(s) 610.

Again, addition of therapeutic agents may be desired. If one or more therapeutic agents are desired, the therapeutic agents are added to the barrier device 100 (step 880). The therapeutic agents may be applied to the barrier device 100 by, for example, pouring or spraying the therapeutic agents onto the barrier device 100.

The barrier device is then removed from the surface (step 882) and the release agent is washed away (step 884).

After removing the barrier device 100 from the surface, one or more therapeutic agents may be added. If therapeutic agents are desired to be added, the therapeutic agents are added to the barrier device 100. In either case, the barrier device 100 is sterilized (step 888).

As with the method of FIG. 7, if desired, a therapeutic agent can be added to the oil component at any point along the process forming the barrier device 100, including being incorporated into the oil component. As discussed previously, consideration must be given as to whether the therapeutic agent may be affected by the curing process, or other aspects of the process.

Furthermore, the formation of the oil component can be done in accordance with different alternatives to the methods described. For example, prior to forming the barrier component 120, a preservative and/or compatibilizer, such as Vitamin E can be mixed with the oil component (e.g., an oil composition). A solvent can be mixed with a therapeutic agent, and then added to the oil to form the oil composition. The solvent can be chosen from a number of different alternatives, including ethanol or N-Methyl-2-Pyrrolidone (NMP). The solvent can later be removed with vacuum or heat.

In addition, it should again be noted that the oil component can be added multiple times to create multiple tiers in forming the barrier component 120. If a thicker barrier component 120 is desired, additional tiers of the oil component can be added after steps 874 and 876. Different variations relating to when the oil component is hardened and when other substances are added to the oil component are possible in a number of different process configurations. Accordingly, the present invention is not limited to the specific sequence illustrated. Rather, different combinations of the basic steps illustrated are anticipated by the present invention.

Depending on the type of therapeutic agent component added to the barrier device 100, the resulting barrier device 100 can maintain its bio-absorbable characteristics if the therapeutic agent component is also bio-absorbable.

The therapeutic agent component, as described herein, has some form of therapeutic or biological effect. The oil component can also have a therapeutic or biological effect. Specifically, the barrier component 120 (and its oil constituents) can enable the cells of body tissue of a patient to absorb the barrier component 120 itself, rather than breaking down the barrier component 120 and disbursing by-products of the barrier component 120 for ultimate elimination by the patient's body.

Figure 9A:
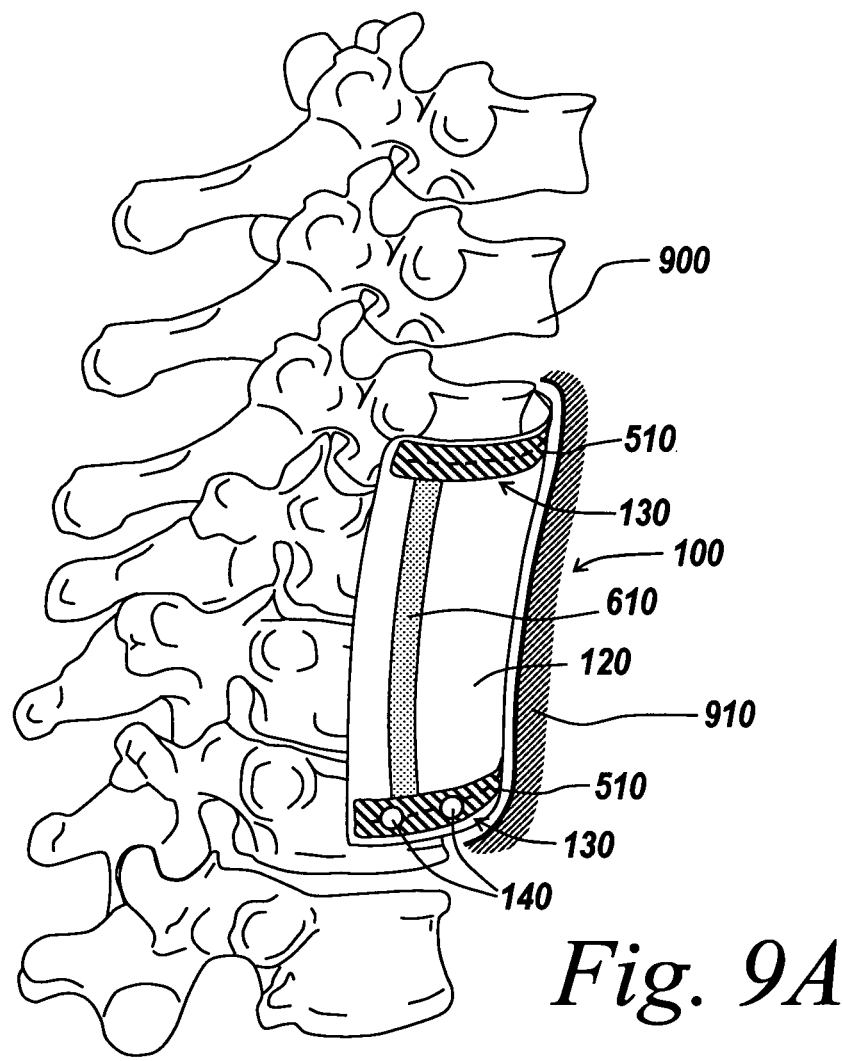
FIGS. 9A-B depict exemplary applications of exemplary barrier devices.

FIG. 9A illustrates one exemplary application for the barrier device 100. The barrier device 100 can be used after spinal surgery to create a physical and biological barrier between a patient's vertebrae 900 and adjacent soft tissue 910. The barrier device 100 can be held in place using an anchoring mechanism, such as adhesive, a suture, a staple, a tack, or any other anchoring or fastening devices that is applied at anchoring locations 130, which may include openings 140 and/or anchor elements 510. The anchor elements 510 can be provided to reinforce the anchoring locations 130. As the patient's spinal membrane heals, the barrier device 100 breaks down and is absorbed by the patient. The barrier device can also include the truss structure 610 to provide additional support to the barrier component 120 of the barrier device 100. The barrier device 100 remains held in position for a period of time that is long enough for the spinal membrane to substantially heal.

Figure 9B:
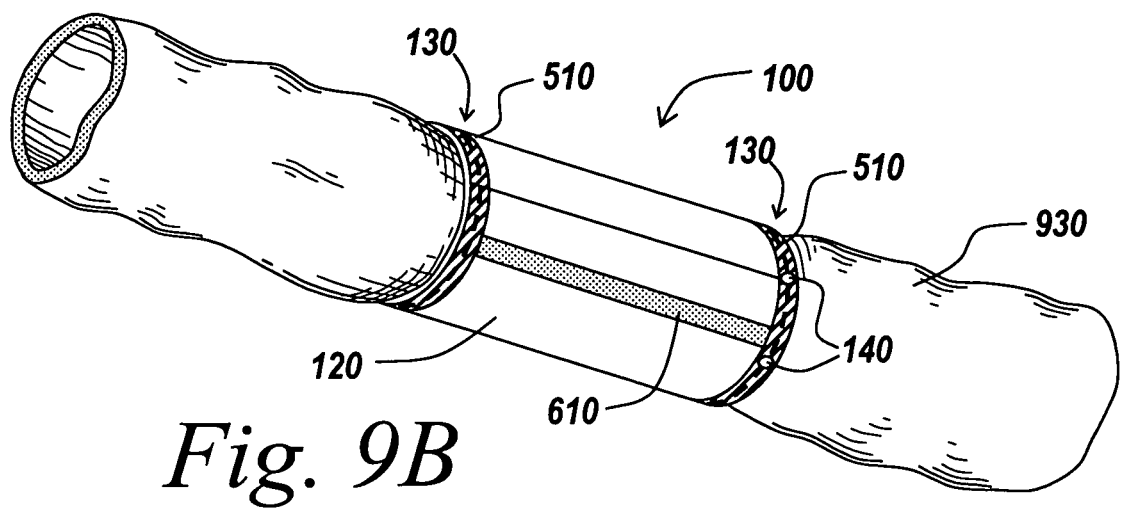

FIG. 9B illustrates another exemplary application for the barrier device 100. The barrier device 100 can be implanted in a patient to substantially encompass a section of the bowels 930 of a patient. Since the barrier device 100 is flexible it can be wrapped around the section of the bowel 930. The anchoring locations 130 can include openings 140 and/or anchor elements 510. The anchor elements 510 can be provided to reinforce the anchoring locations 130 for attaching the barrier device 100 to the bowels 930 as well as to itself. The truss structure 610 can be disposed on the barrier device to provide additional support to the barrier component 120.

As previously stated, and in accordance with embodiments of the present invention, the barrier component 120 is formed of a biocompatible oil, or composition including a naturally occurring oil, such as fish oil, cod liver oil, cranberry oil, and the like, or a synthetic oil including at least the required fatty acids and lipids in accordance with characteristics of the natural oils. A characteristic of the biocompatible oil is that the oil includes lipids, which contributes to the lipophilic action described later herein, that is helpful in the delivery of therapeutic agents to the cells of the body tissue. In addition, the biocompatible oil can include the essential omega-3 fatty acids in accordance with several embodiments of the present invention.

It should also be noted that the present description makes use of the anchor element(s) and/or truss structure(s) as an example of medical devices that can be combined with the barrier component 120. However, the present invention is not limited to use with the anchor element(s) and/or truss structure(s). Instead, any number of other implantable medical devices can be combined with the barrier component in accordance with the teachings of the present invention. Such medical devices include catheters, grafts, balloons, prostheses, stents, other medical device implants, and the like. Furthermore, implantation refers to both temporarily implantable medical devices, as well as permanently implantable medical devices.

The barrier device 100 with their anchor elements and/or truss structures as described herein all further exhibit a feature that greatly improves visibility of the barrier device 100 during an implantation procedure. Specifically, through the light transmitting properties of the barrier component 120, and specifically through the characteristics of the oil-based material that is utilized to form the barrier component 120, the edges of the barrier device 100 are illuminated when a light is applied to the barrier device 100. Specifically, when a light is provided at various angles to illuminate an area during a surgical operation, including implantation of a barrier device 100, the light translates through the barrier component 120 and at any cut or otherwise terminating edge, the edge is illuminated in a manner that outlines or highlights the edge relative to the other portions of the barrier device 100. This illumination of the edges of the barrier device 100 makes it easier for a surgical user to find the edges and know where the reinforcing anchor elements are placed, due to the light that outlines or highlights the relevant edges.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:
1. An implantable medical barrier device, comprising:
a barrier component having a perimeter defined by at least one pair of opposing edges, and a surface extending between the opposing edges, the barrier component comprising a cured fish oil, wherein the fish oil comprises eicosapentaenoic acid and docosahexanoic acid, wherein the cured fish oil comprises fatty acids and glycerides, wherein the fatty acids are reversibly cross-linked to each other in a substantially random configuration to form a three dimensional hydrolytically degradable network, and wherein the barrier compo- nent is bio-absorbable and breaks down in vivo into non-inflammatory substances consumable by tissue cells; and an anchoring location formed at least one of on, in, or about the surface of the barrier component and comprising a biocompatible mesh, the at least one anchoring location occupying a first area that is less than an area of the barrier component.

2. The device of claim 1, wherein the biocompatible mesh facilitates an anchoring of the barrier device to an anatomical area.

3. The device of claim 1, wherein the biocompatible mesh is disposed along a perimeter of the barrier component.

4. The device of claim 3, wherein the biocompatible mesh forms a continuous frame along the perimeter of the barrier component.

5. The device of claim 1, wherein the barrier component has a non-circular shape.

6. The device of claim 1, wherein the cured fish oil is a partially cured fish oil.

7. The device of claim 1, wherein the barrier component comprises at least one therapeutic agent component.

8. The device of claim 7, wherein the therapeutic agent component comprises an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

9. The device of claim 1, wherein the barrier component comprises a plurality of tiers.

10. The device of claim 9, wherein the barrier component comprises a first tier and a second tier configured on the first tier, wherein the first tier is cured to a greater extent than the second tier.

11. The device of claim 1, wherein the barrier component comprises an oil composition that includes fish oil in combination with at least one component selected from the group consisting of an additional oil component, a therapeutic agent component, a solvent, and a preservative.

12. The device of claim 1, wherein the barrier component further comprises alpha tocopherol or a derivative or analog thereof.

13. The device of claim 1, wherein the device is configured for implantation in a bowel region.

14. The device of claim 1, wherein the barrier component has a circular shape.

15. The device of claim 1, wherein the barrier component is a standalone film that is completely absorbed into surrounding tissue.

16. An implantable medical barrier layer device, comprising:

a barrier component having a perimeter defined by at least one pair of opposing edges, and a surface extending between the opposing edges, the barrier component comprising a cured fish oil, wherein the fish oil comprises eicosapentaenoic acid and docosahexanoic acid, wherein the cured fish oil comprises fatty acids and glycerides, wherein the fatty acids are cross-linked to each other in a substantially random configuration to provide a three-dimensional hydrolytically degradable network of a bio-absorbable and anti-adhesive film, and wherein the barrier component breaks down in vivo into non-inflammatory substances consumable by tissue cells;

at least one anchor element coupled to the barrier component, the at least one anchor element comprising a biocompatible material and having an area that is less than the area of the barrier component to provide an anchoring location on the barrier device for anchoring the barrier layer to an anatomical area; and a truss structure that extends across a non-perimeter portion of the surface between the opposing edges of the barrier component and toward the perimeter of the barrier component to provide additional support to the barrier component;

wherein the truss structure contacts the perimeter.

17. The device of claim 16, wherein the truss structure comprises a biocompatible material.

18. The device of claim 16, wherein the barrier component is a standalone film that is completely absorbed into surrounding tissue.

19. An implantable medical barrier device, comprising:

a standalone film having a perimeter defined by at least one pair of opposing edges, and a gliding surface extending between the opposing edges, wherein the standalone film comprises a cured fish oil having cross-linked fatty acids, wherein the standalone film is bio-absorbable and breaks down in vivo into non-inflammatory substances consumable by tissue cells so that the standalone film is completely absorbed; and an anchoring location formed on the gliding surface of the standalone film, or in the gliding surface of the standalone film, or on and in the gliding surface of the standalone film, wherein the at least one anchoring location occupies a first area that is less than a total area of the standalone film.

20. The device of claim 19, wherein the cured fish oil forming the standalone film modulates healing so that substantially no fibrous capsule forms on the standalone film during healing.

21. The device of claim 19, wherein the anchoring location comprises a biocompatible mesh at least partially encapsulated by the standalone film.

22. The device of claim 21, further comprising:

a truss structure that extends across a non-perimeter portion of the surface between the opposing edges of the standalone film and toward the perimeter of the standalone film to provide additional support to the standalone film, wherein the truss structure contacts the perimeter.

23. The device of claim 19, wherein the anchoring location comprises an opening formed through the standalone film.

* * * * *